(12) United States Patent
Alden

(10) Patent No.: US 11,622,869 B2
(45) Date of Patent: Apr. 11, 2023

(54) FEMORAL COMPONENT EXTRACTOR

(71) Applicant: Tri-Sphere Holdings, LLC, Osprey, FL (US)

(72) Inventor: Dana Andrew Alden, Osorey, FL (US)

(73) Assignee: Tri-Sphere Holdings, Osprey, FL (US)

( * ) Notice: Subject to any disclaimer, the term of this patent is extended or adjusted under 35 U.S.C. 154(b) by 0 days.

(21) Appl. No.: 16/525,492

(22) Filed: Jul. 29, 2019

(65) Prior Publication Data
US 2021/0030563 A1  Feb. 4, 2021

(51) Int. Cl.
*A61F 2/46* (2006.01)
*A61B 17/92* (2006.01)

(52) U.S. Cl.
CPC .......... *A61F 2/4607* (2013.01); *A61B 17/921* (2013.01); *A61F 2002/4619* (2013.01); *A61F 2002/4629* (2013.01); *A61F 2002/4681* (2013.01)

(58) Field of Classification Search
CPC .......... A61B 17/921; A61B 2002/4619; A61F 2002/4628; A61F 2/4607; A61F 2002/4681; B25B 27/02; B25B 27/023; B25B 27/062; Y10T 24/44291; F16B 2/10; F16B 2/065
See application file for complete search history.

(56) References Cited

U.S. PATENT DOCUMENTS

| | | | | |
|---|---|---|---|---|
| 1,590,159 A | * | 6/1926 | Gillentine | B25B 27/005 29/261 |
| 2,376,375 A | * | 5/1945 | Mizer | B25B 27/023 29/256 |
| 2,834,100 A | * | 5/1958 | Harsh | B25B 27/023 29/261 |
| 4,084,305 A | * | 4/1978 | Chang | B25B 27/023 29/261 |
| 4,222,382 A | * | 9/1980 | Antonsson | A61F 2/4607 606/100 |

(Continued)

FOREIGN PATENT DOCUMENTS

EP  3799841 A1 *  4/2021  ............. A61B 17/92

OTHER PUBLICATIONS

Shukla Medical; Shukla Hip Universal Hip Implant Extraction Solution and MOD Shukla Hip Universal Hip Implant Extraction Solution; 2002. esp. p. 10, 11, 13 (Year: 2002).*

(Continued)

*Primary Examiner* — David W Bates

(57) ABSTRACT

The invention is defined by the claims set forth herein; however, briefly, the invention herein is an extractor for a human femoral component with a trunnion neck comprising, a plurality of extractor sections, including a first section with a first axis, a second section with a second axis, and a third section with a third axis; a body with a threaded hole defined therein that is provided with a clamping body section and a central body section, a pivoting member with first end, a second end, and a pivot hole defined therebetween that includes a clamping structure located at the second end that is shaped to clamp the trunnion neck of the femoral component; and a pivot that secures the pivoting member to the body by extending through the pivot hole defined in the pivoting member and the pivot hole defined in the fulcrum structure of the body.

25 Claims, 23 Drawing Sheets

SECTION A-A
SCALE 1:2

(56) References Cited

U.S. PATENT DOCUMENTS

| | | | | |
|---|---|---|---|---|
| 4,601,289 | A * | 7/1986 | Chiarizzio | A61B 17/1659 606/85 |
| 4,869,482 | A * | 9/1989 | Beccaceci | B25B 27/023 269/239 |
| 4,993,410 | A * | 2/1991 | Kimsey | A61F 2/4607 606/100 |
| 5,007,155 | A * | 4/1991 | Jordan | B25B 27/023 29/434 |
| 5,064,427 | A * | 11/1991 | Burkinshaw | A61F 2/4612 606/99 |
| 5,514,136 | A * | 5/1996 | Richelsoph | A61F 2/4607 606/99 |
| 5,534,006 | A * | 7/1996 | Szabo | A61F 2/4607 606/100 |
| 5,735,857 | A * | 4/1998 | Lane | A61B 17/8872 606/207 |
| 5,743,910 | A * | 4/1998 | Bays | A61F 2/4607 606/99 |
| 5,906,034 | A * | 5/1999 | Weisshaar | B25B 27/023 269/93 |
| 5,951,564 | A * | 9/1999 | Schroder | A61F 2/4607 606/100 |
| 5,960,689 | A * | 10/1999 | Warren | B25B 27/02 82/903 |
| 7,022,141 | B2 | 4/2006 | Dwyer | A61F 2/4657 623/22.12 |
| 8,085,481 | B2 * | 12/2011 | Hill | G03B 3/00 248/230.4 |
| 8,690,880 | B2 * | 4/2014 | Bastian | A61B 17/164 606/85 |
| 9,089,440 | B2 * | 7/2015 | Mueller | A61F 2/461 |
| 9,273,821 | B2 * | 3/2016 | Chang | F16M 11/041 |
| 9,351,565 | B2 * | 5/2016 | Torrachi | F16B 2/065 |
| 9,526,512 | B2 * | 12/2016 | Sharp | A61B 17/164 |
| 2,019,169 | A1 | 6/2019 | Alden | |
| 10,987,231 | B2 * | 4/2021 | Sweitzer | A61F 2/461 |
| 2008/0033444 | A1 * | 2/2008 | Bastian | A61B 17/1668 606/85 |
| 2008/0172061 | A1 * | 7/2008 | Ragbir | A61F 2/4603 606/99 |
| 2008/0262503 | A1 * | 10/2008 | Muller | A61F 2/4612 606/99 |
| 2014/0207123 | A1 * | 7/2014 | Mueller | A61F 2/4607 606/1 |
| 2015/0267863 | A1 * | 9/2015 | Chang | F16M 13/00 248/333 |
| 2018/0028249 | A1 * | 2/2018 | Jaumard | A61F 2/4607 |
| 2018/0187704 | A1 * | 7/2018 | Chang | F16M 11/041 |
| 2019/0336307 | A1 * | 11/2019 | Sungu | A61F 2/3662 |
| 2020/0291973 | A1 * | 9/2020 | Gassaway | F16B 1/00 |

OTHER PUBLICATIONS

Stryker; Rejuvenate Total Hip System Surgical Protocol; 2011. p. 14 (Year: 2011).*
International Search Report for PCT/US2020/000029, dated Oct. 2020 (Year: 2020).*
Innomed, Innovations in Orthopedic Instruments, 2016 (Year: 2016).*
Lafosse, J., M. Removal of well-fixed femoral stems; Elsevier. 2015 (Year: 2015).*
DePuy extractor manufactured and sold before the filing date of U.S. Appl. No. 16/525,492. Photographs attached.

* cited by examiner

DETAIL A
SCALE 1:1

SECTION A-A
SCALE 1:2

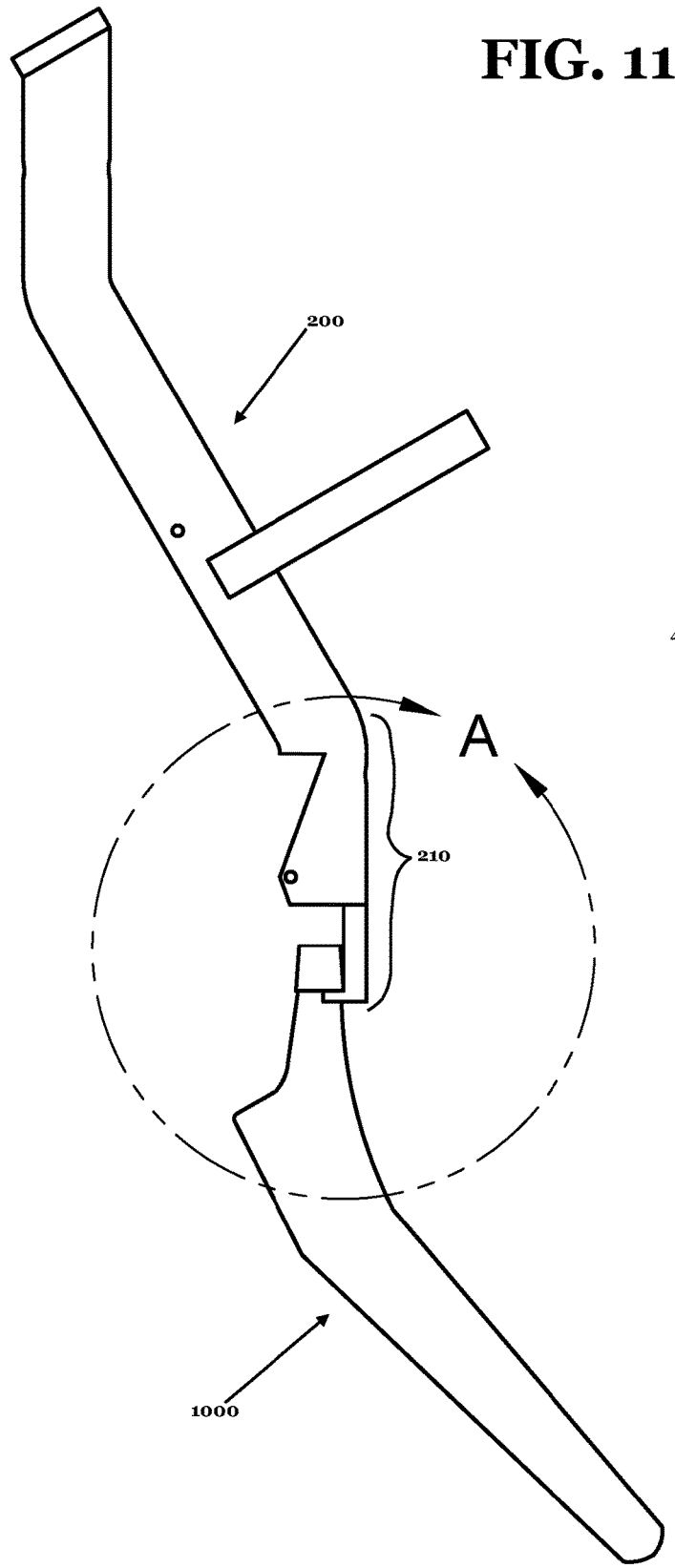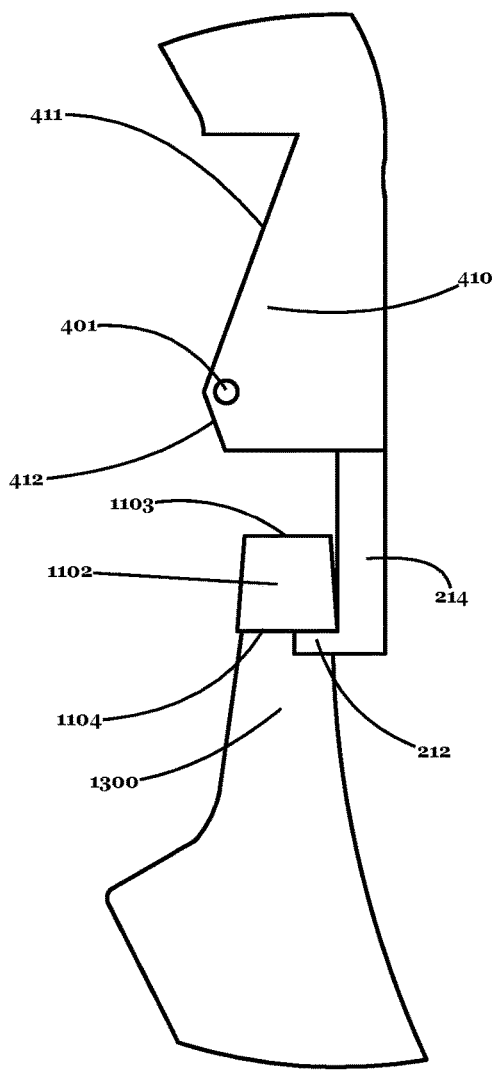
FIG. 11
DETAIL A
SCALE 1:1

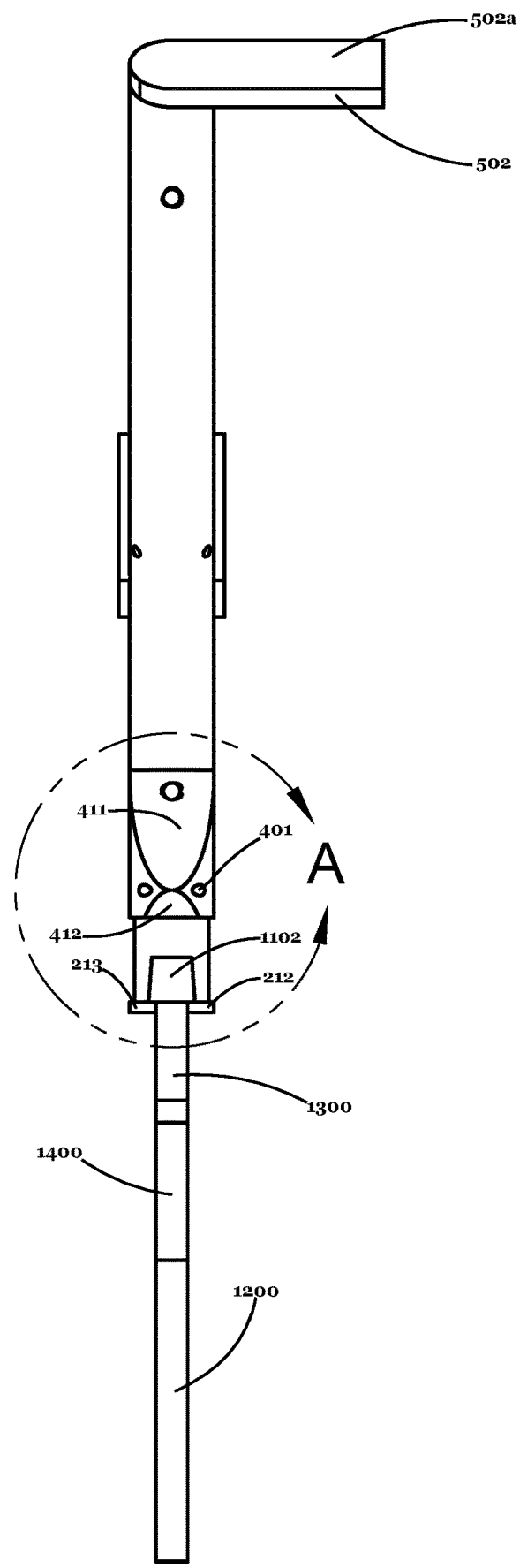
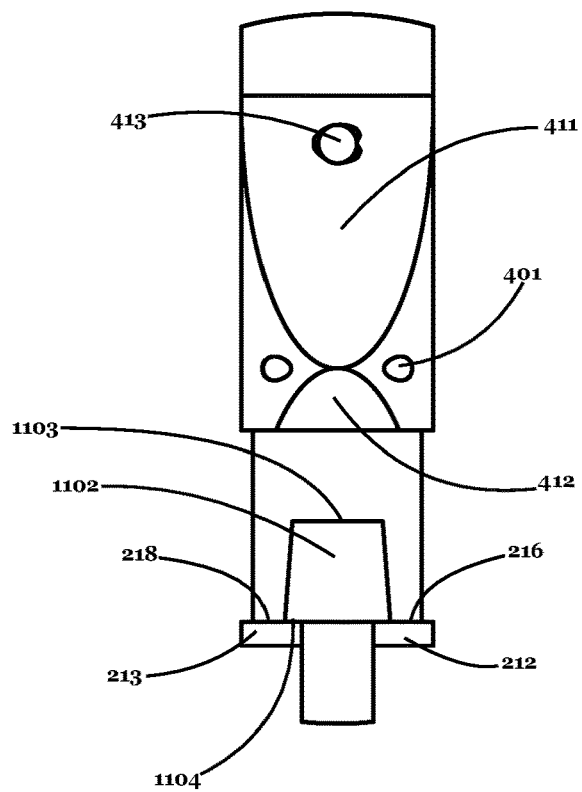
FIG. 12
DETAIL A
SCALE 1:1

SECTION A-A
SCALE 1:2

SECTION A-A
SCALE 1:2

FEMORAL COMPONENT EXTRACTOR

FIELD OF THE INVENTION

This patent application relates to surgical instruments used to extract the femoral component of an artificial hip.

BACKGROUND OF THE INVENTION

It has been known in orthopedic surgical practices to implant artificial hips. Such prosthetic devices include a femoral component and an acetabular component, which together function as a ball and socket joint. The femoral component is often fabricated from metallic biomaterials with a surface finish that is highly polished. The smooth surfaces of the femoral component inhibit corrosion and bacterial growth. FIG. 8 of the drawings provided herein depicts such a femoral component, and, as shown, the femoral component includes a stem provided with an axis and a spherically-shaped head that extends from the axis of the stem at an irregular angle (i.e. an angle that is not 90 degrees).

The stem is shaped to be inserted axially into a patient's femur. Naturally, before the femoral component can be implanted, the patient's existing femoral head must be removed and the femur prepared to receive the prosthesis. The surgeon accomplishes this by broaching a cavity within the femoral canal that is shaped according to the stem. Often, surgeons undersize the cavity and impact the femoral component into the femur so that the prosthesis is firmly secured without any voids where bacteria and other infection causing agents can grow. Alternatively, surgeons fill the cavity with a type of cement and then fix the stem of the femoral component within the cement.

Unfortunately, artificial implants loosen, components corrode and break, bio-compatibility degrades, and infections develop. Thus, patients with artificial hips sometimes require hip revision surgery. In such a procedure, the prosthetic implants must be removed, including the femoral component. However, as noted above, the femoral component is often well-fixed within the patient's femur. As noted above, the irregular geometric configuration combined with the polished surfaces render vice-grip instruments largely ineffective as they slip on the femoral component's smooth surfaces.

If the femoral component cannot be extracted, the surgeon must remove the femoral component surgically via an extended trochanteric osteotomy, a procedure that often has complications and extends patient recovery. Thus, there is a need for an extractor that can clamp onto the polished surfaces of the femoral component without slipping. There is also a need for an extractor that can remove a femoral component despite the irregular geometry associated with such prosthetic devices. There is also a need for an extractor that enables a surgeon to impact a well-fixed femoral component from a patient's femur without resorting to additional surgical procedures that have complications of their own and that extend a patient's recovery time.

The foregoing does not purport to be an exhaustive explication of all the disadvantages associated with prior art extractors; however, the present invention is directed to overcoming these (and other) disadvantages inherent in prior art systems. The advantages of the present invention will become readily apparent to those of ordinary skill in the art after reading the disclosure provided herein.

BRIEF DESCRIPTION OF THE DRAWINGS

FIG. 11 depicts a perspective view of the body of the extractor with the neck of a femoral component located between the arms of the body.

FIG. 12 depicts a detailed view of the body of the extractor with the neck of the femoral component located between the arms of the body.

SUMMARY OF THE INVENTION

The invention is defined by the claims set forth herein; however, briefly, the invention herein is an extractor for a femoral component with a trunnion neck comprising, a plurality of extractor sections, including a first section with a first axis, a second section with a second axis, and a third section with a third axis; a body with a threaded hole defined therein that is provided with a clamping body section and a central body section, a pivoting member with first end, a second end, and a pivot hole defined thereinbetween that includes a clamping structure located at the second end that is shaped to clamp the trunnion neck of the femoral component; and a pivot that secures the pivoting member to the body by extending through the pivot hole defined in the pivoting member and the pivot hole defined in the fulcrum structure of the body.

DETAILED DESCRIPTION OF THE INVENTION

Figure 1:
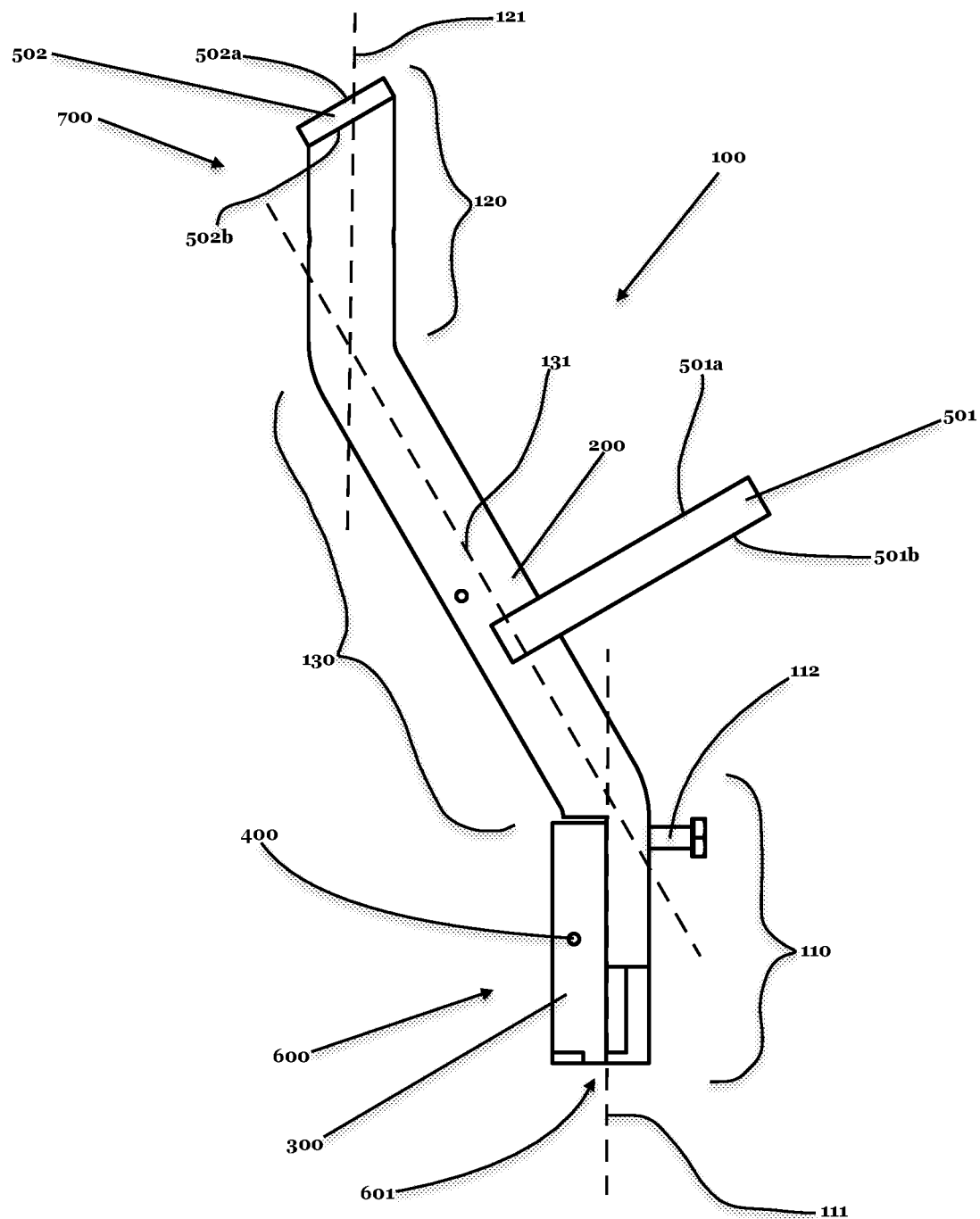
FIG. 1 depicts a perspective view from one side of the extractor.

FIG. 1 depicts an extractor 100 constituting a presently preferred embodiment of the invention disclosed herein. The extractor 100 is provided with a body 200 with a pivoting member 300 and a strike plate (preferably a plurality of strike plates 501, 502, as is shown in FIG. 1). A pivot 400 in the form of a stainless steel pin secures the pivoting member 300 to the body 200. The body 200, the pivoting member 300, the strike plates 501, 502, and the pivot 400 are preferably manufactured from a stainless steel, such as the 300 or 400 grade stainless steels (e.g. 304, 316, and 416 stainless steel); however, in an alternative embodiment, the body 200, the pivoting member 300, the strike plates 501, 502, and the pivot 400 are manufactured from titanium.

Each of the strike plates 501, 502 (referred to as a "first strike plate 501" and a "second strike plate 502" to distinguish one from the other) is provided with an upper striking surface (designated 501a and 502a) and a lower striking surface (designated 501b and 502b). Also shown in FIG. 1, the extractor 100 is provided with a first end 600 and a second end 700, as well as a plurality of extractor sections 110, 120, 130, each of which includes an axis designated 111, 121, 131 respectively. FIG. 1 depicts the extractor 100 with a first section 110 (also referred to as a "clamping section 110") with a first axis 111 (also referred to as a "clamping axis 111"), an upper extractor section 120 with an upper axis 121, and a central extractor section 130 with a central axis 131.

As FIG. 1 illustrates, the upper axis 121 and the clamping axis 111 are generally parallel in orientation. As FIG. 1 also shows, the first end 600 terminates at an opening 601 that is formed by the pivoting member 300 and the body 200, while the second end 700 terminates at the second strike place 502. FIG. 1 further depicts the extractor 100 provided with a threaded component 112 that engages with internal threads located within the body 200. In the preferred embodiment, the threaded component 112 is a hex bolt (and therefore is provided with threaded shank and a torque transferring structure in the form of a hex head). One of ordinary skill in the art will appreciate that a hex bolt is not necessary; in an alternative embodiment, the extractor 100 is provided with a threaded T-bar wherein the torque transferring structure is a T-handle.

Figure 2:
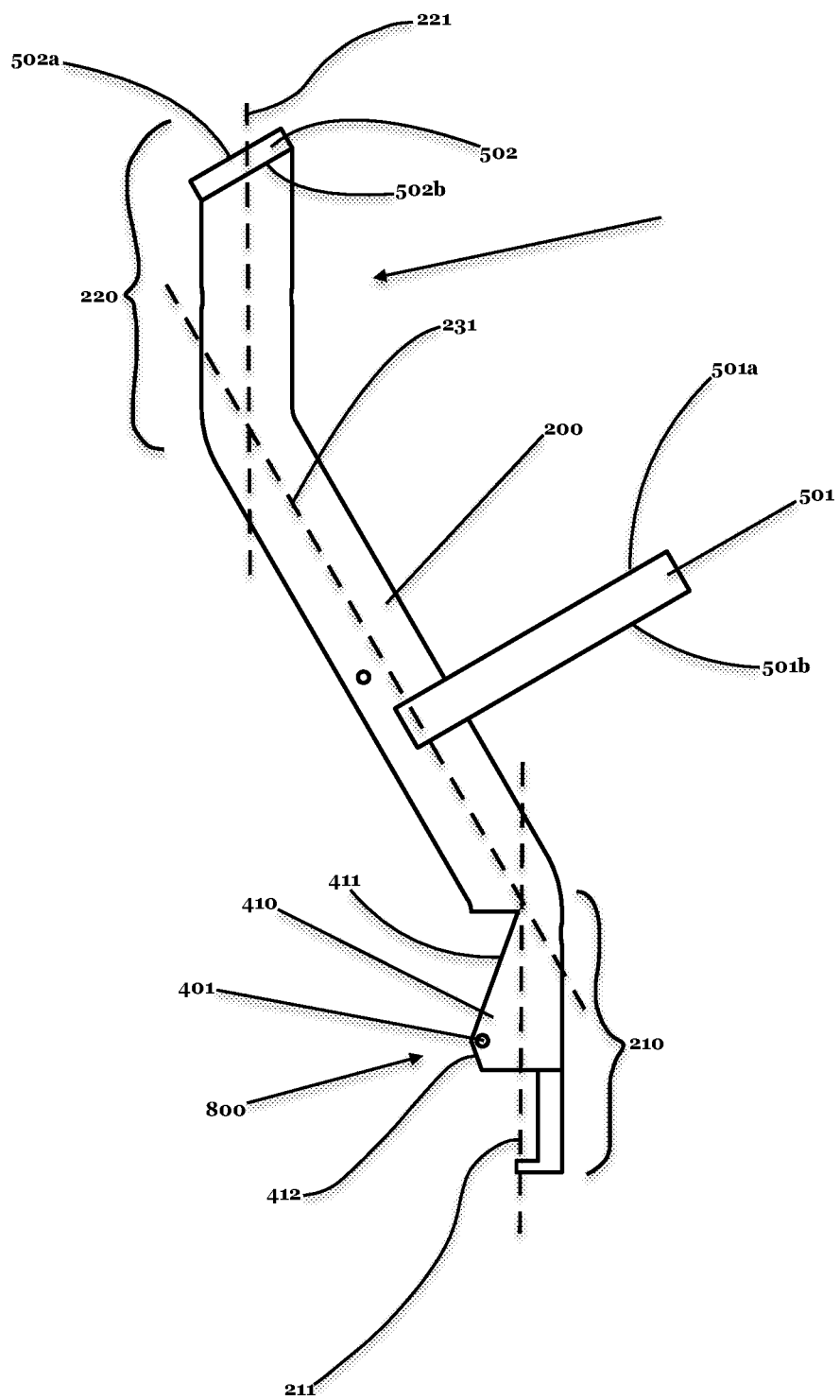
FIG. 2 depicts a perspective view from one side of the body of the extractor.

Referring now to FIG. 2, the body 200 of the extractor 100 is shown. As depicted therein, the body 200 is provided with first and second ends 800, 900 respectively. The first and second ends 800, 900 of the body 200 generally correspond to the first and second ends of the extractor 100. The body 200 is provided with an angled section, preferably a plurality of angled section; accordingly, the body shown in FIG. 2 includes a first angled section, more specifically referred to herein as a clamping body section 210, and a second angled section 220, more specifically referred to herein as an impacting body section. Located between the angled sections 210, 220, a central body section 230 is included within the body 200. As FIG. 2 also shows, each of the section is provided with an axis. The clamping body section 210 is provided with a clamping body axis 211; the impacting body section 220 is provided with an impacting body axis 221, and the central body section 230 is provided with a central body axis 231. As is evident in the figures, the clamping body axis 211 and the impacting body axis 221 are generally parallel to each other.

In the preferred embodiment, the body 200 is generally cylindrical in shape (and hence provided with a generally circular cross-sectional shape). However, one of ordinary skill in the art will appreciate that other cross-sectional shapes are within the scope of the present invention. By way of example (and not limitation), it is permissible for the body to be rectangular in shape (and hence have a square or rectangular cross-sectional shape). In an alternative embodiment, the body 200 is fabricated from hexagonal bar stock, which provides a hexagonal cross-sectional shape. In such an embodiment, the body 200 is provided with a polygonal cross-sectional shape. Thought he preferred embodiment is fabricated from round bar stock, alternative embodiments are fabricated from semi-circular bar stock.

Much like the extractor 100, the various sections 210, 220, 230 of the body 200 are each provided with an axis. FIG. 2 illustrates that the body 200 is provided with a plurality of axes, including a central body axis 231, an impacting body axis 221, and a clamping body axis 211.

Figure 3:
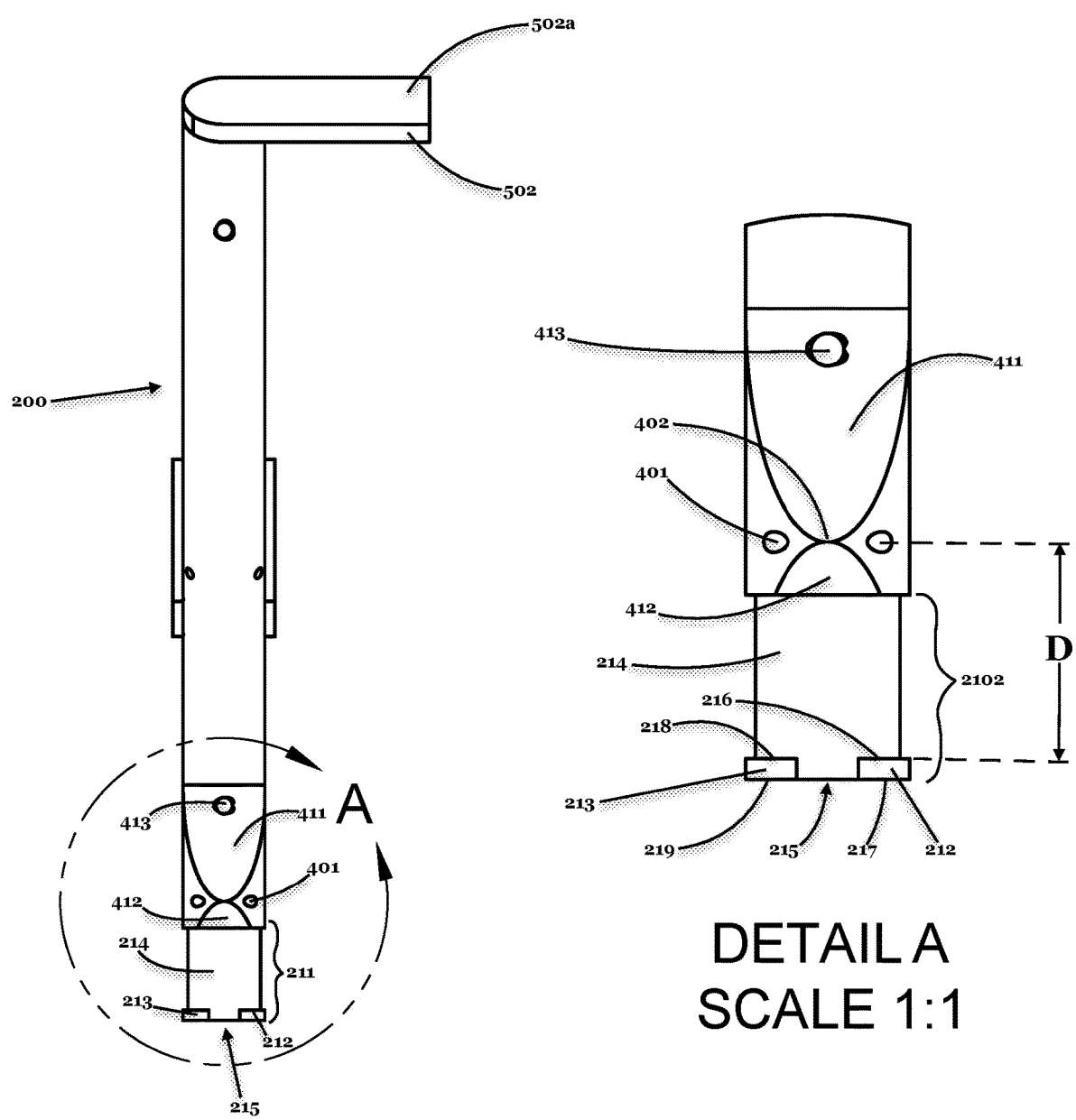
FIG. 3 depicts a detailed view of an end of the body of the extractor.

FIG. 3 depicts the first section 210 of the body 200 in greater detail. As shown therein, the first section is provided with a plurality of through holes, including a pivot hole 401 and a threaded hole 413. The pivot hole 401 and the threaded hole 413 are oriented to be generally orthogonal to each other. The first end 210 of the body 200 is milled to provide a fulcrum structure 410 with an angled fulcrum surface 411. The angled fulcrum surface 411 extends from the pivot hole 401 in a direction that is both radially inward towards the axis 11 of the extractor 100 (shown in FIG. 1) and axially towards the second end 220 of the body 200 so that the fulcrum surface 411 is oriented at an angle 414 (shown in FIG. 7) relative to the axis 111 of the first extractor section 110. In the preferred embodiment, this angle 414 measures 20 degrees relative to the axis 111.

The angled fulcrum surface 411 terminates (at least in part) at a tightening surface 412. The tightening surface 412 extends radially inward towards the axis 111 of the first end 110 of the extractor 100 and axially away from the second end 220 of the body 200 so that the plane of the tightening surface 412 is at an angle relative to the clamping body axis 211 that measures 20 degrees. The tightening surface 412 terminates where the body 200 provides a trunnion accepting structure 2102.

The trunnion accepting structure 2102 is provided with an arm extension bar 214 and a pair of arms 212, 213. From where the tightening surface 412 terminates, the arm extension bar 214 extends axially so as to accommodate the axial dimension of the trunnion of the femoral component between the tightening surface 412 and the arms 212, 213. Each of the arms 212, 213 extends from the arm extension bar 214 so that each is generally parallel to the other. The arms 212, 213 are spaced from each other so as to define a notch 215 dimensioned according to a diameter of the trunnion of the femoral component; in the embodiment shown herein, the arms 212, 213 are spaced less than 0.55 inches, preferably between 0.5 inches and 0.375 inches, from each other, inclusively.

As FIG. 3 also illustrates, the arms 212, 213 are provided with upper arm surfaces 216, 218 and lower arm surfaces 217, 219. The upper arm surfaces 216, 218 are spaced axially from the pivot hole 401 at distance designated "D" in FIG. 3. In the preferred embodiment, "D" measures greater than 0.551 inches.

Figure 4:
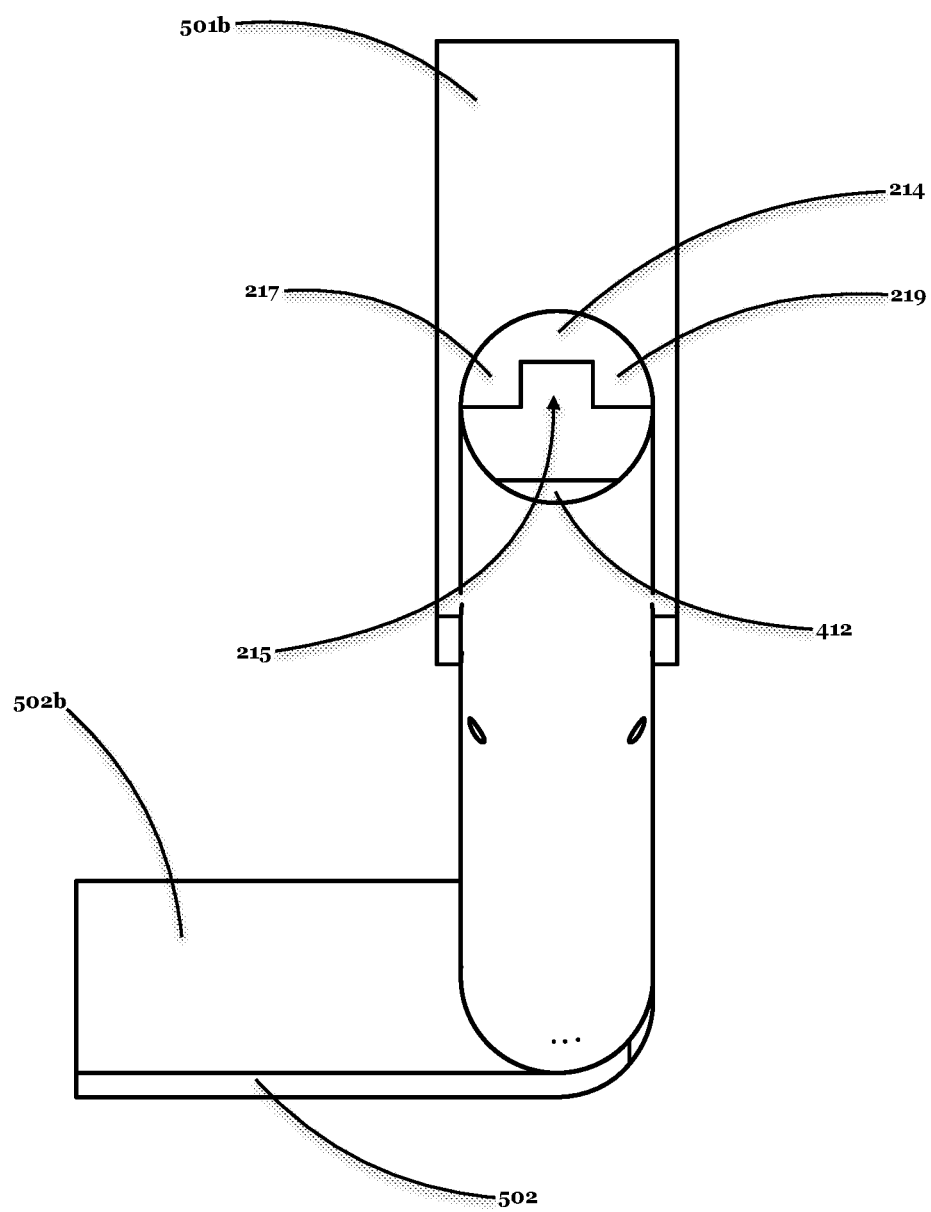
FIG. 4 depicts a perspective view from the bottom of the body.

FIG. 4 depicts a view of the lower arm surfaces 217, 219 extending from the arm extension bar 214 and defining the notch 215 therebetween. The notch 215 is dimensioned to accept, at least in part, the femoral component, preferably the neck of the femoral component.

Figure 5:
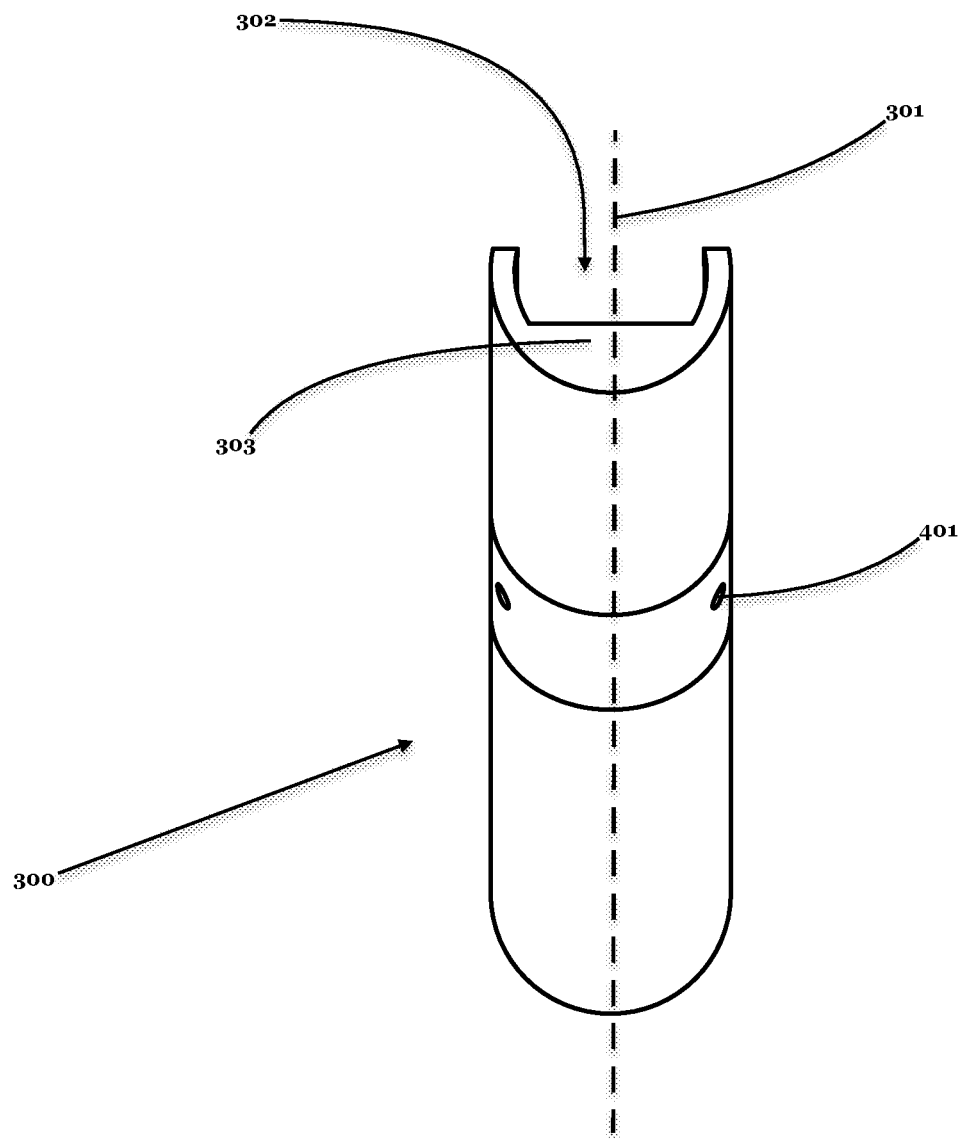
FIG. 5 depicts a perspective view from one side of a pivoting member.
Figure 6:
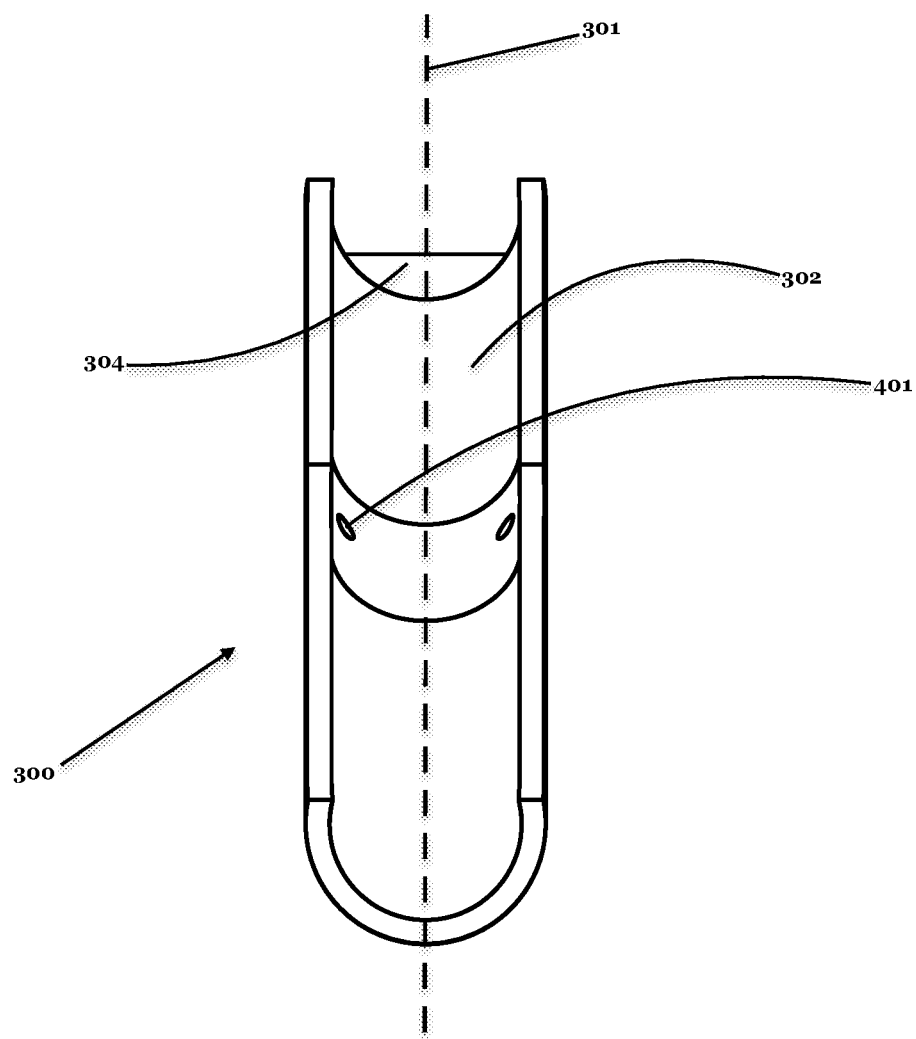
FIG. 6 depicts perspective view of the pivoting member of FIG. 5 from the other side.

Referring now to FIGS. 5 and 6, perspective views of the pivoting member 300 are shown. As both FIGS. 5 and 6 show, the presently preferred pivoting member 300 is in the shape of a cylinder, preferably a half cylinder, with the cylindrically-shaped profile enclosing a pocket 302 and an axis 301 (referred to as the "pivoting axis 301"). The pocket 302 terminates to form a clamping structure 303. As FIG. 6 illustrates, it is preferred that the clamping structure 303 be in the form of a tooth that engages the neck of the femoral component.

In the preferred embodiment, the pivoting member is fabricated from semi-circular bar stock with the pocket 302 milled out through the use of a ball-nose end mill. The hole 401 for the pivot 400 is simply drilled using an appropriately sized drill for a stainless steel pin. While the preferred embodiment is cylindrically-shaped, those with ordinary skill in the art will appreciate that other shapes are within the scope of the present invention. For example, in an alternative embodiment, the pivoting member 300 is fabricated by milling the pocket 302 into rectangular bar stock thereby yielding a pivoting member 300 that is rectangular in shape. In yet another alternative embodiment, the pivoting member 300 is fabricated by milling the pocket 302 from hexagonal bar stock, thereby yielding a pivoting member 300 that is polygonal in shape.

As noted above (and as FIG. 6 illustrates), the clamping structure 303 is in the form of a tooth that is between 0.0625" and 0.25" inches wide inclusively (with the preferred width being 0.125"). Though the clamping structure 303 is in the form of a tooth, those with skill in the art will appreciate that the clamping structure 303 can take other forms and dimensions.

Figure 7:
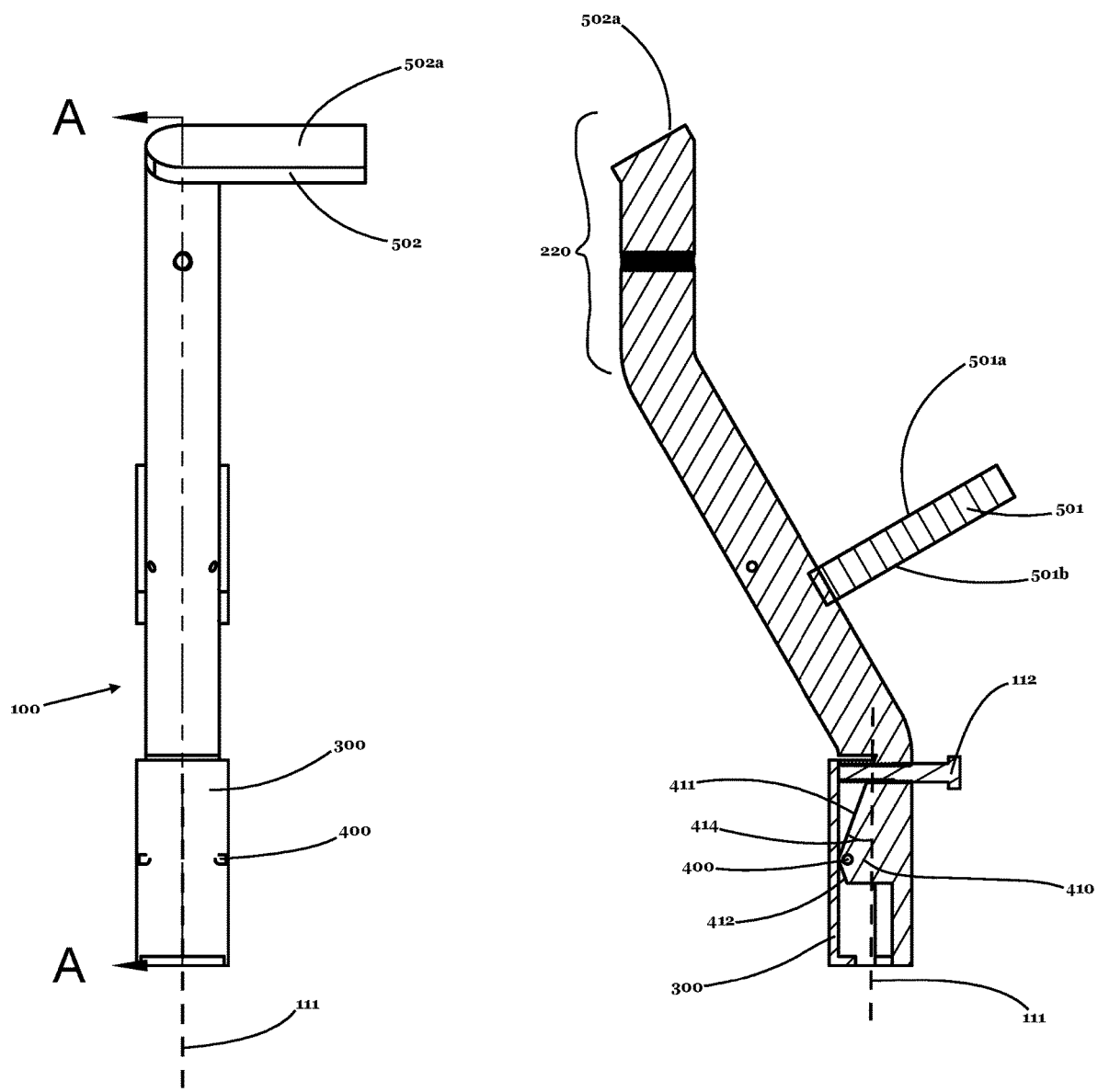
FIG. 7 depicts a sectional view of the extractor.

Turning to FIG. 7, the pivoting member 300 is attached to the body 200 via a pivot 400, which, as noted above, is in the form of a stainless steel pin. FIG. 7 depicts a cross-sectional view of the extractor 100 with the pivoting member 300 so attached. As noted above and as FIG. 7 shows, the fulcrum structure 410 of the body 200 includes the angled fulcrum surface 411 and the tightening surface 412. Consequently, when the pivoting member 300 is attached to the body 200, the pivoting member 300 (and hence the axis 301 of the pivoting member 300) is rotatable on the fulcrum structure 410 of the body 200. Thus, the pivoting member 300 is rotatable so that the axis 301 of the pivoting member 300 is generally parallel with the fulcrum surface 411 (such as when the threaded component 112 is retracted) or generally parallel with the tightening surface 412 (such as when the threaded component 112 is tightened and torqued into the body 200. As noted above, the range of rotation of the pivoting member 300 between the fulcrum surface 411 and the tightening surface 412 is 40 degrees.

Figure 8:
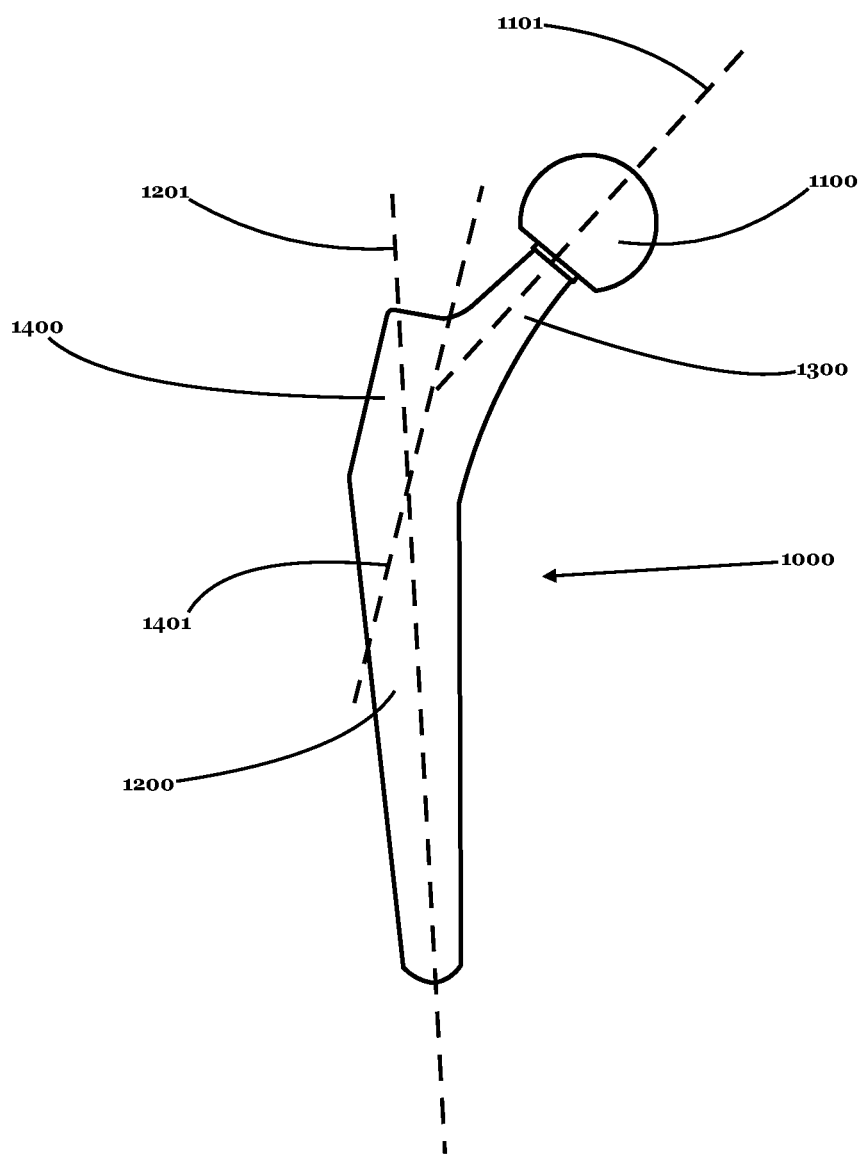
FIG. 8 depicts a perspective view of a femoral component.
Figure 9:
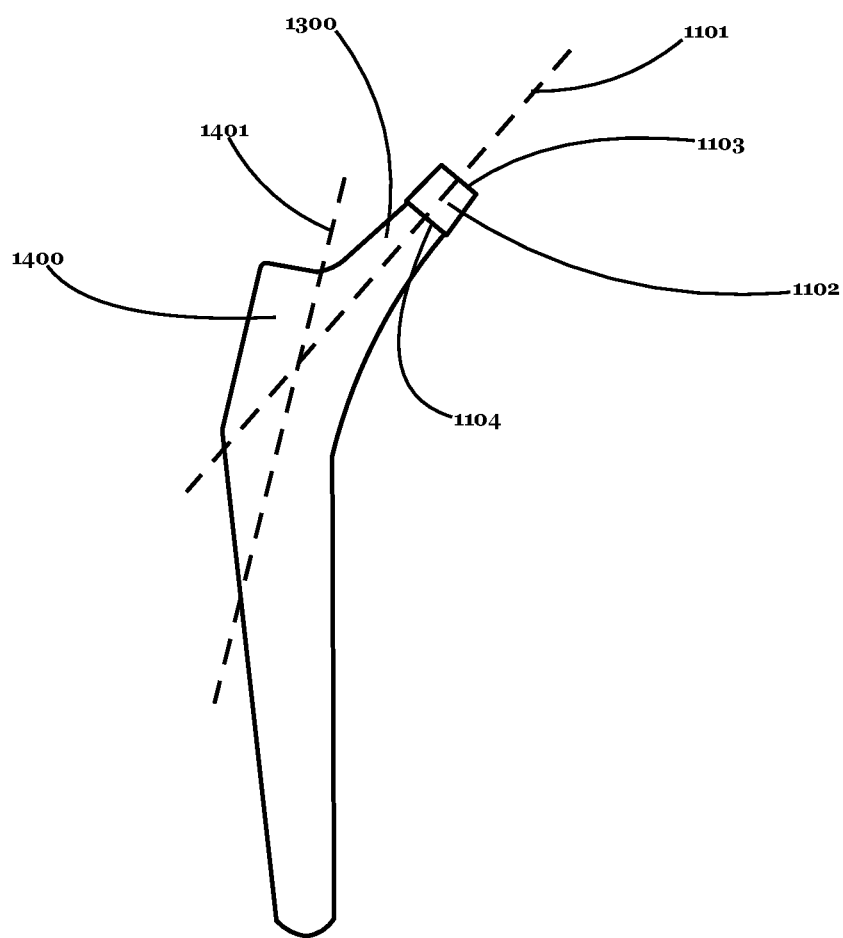
FIG. 9 depicts a perspective view of a femoral component without the head.
Figure 10:
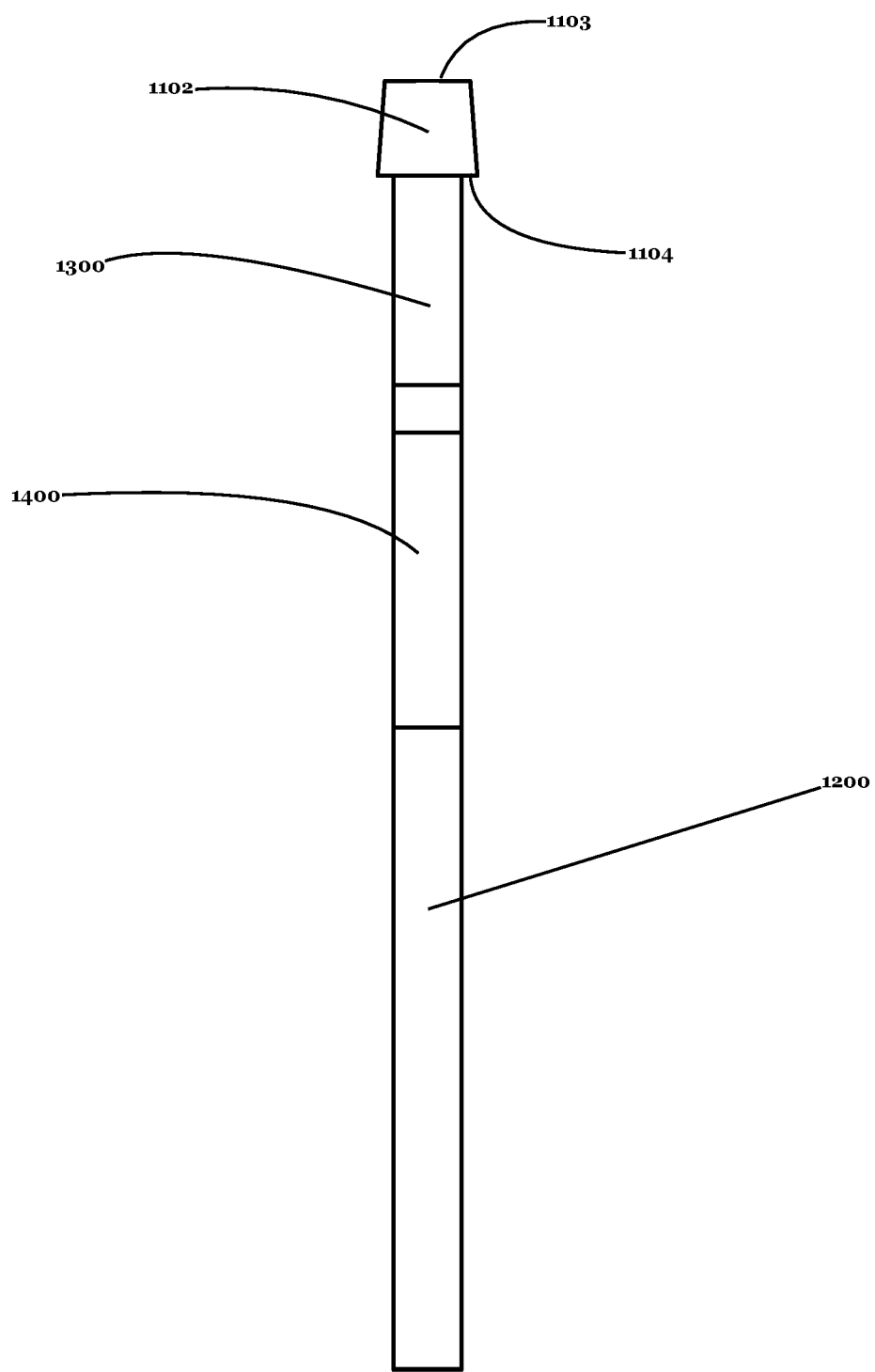
FIG. 10 depicts a perspective view of a femoral component without the head.

As noted above, the extractor 100 is configured to remove a femoral component from a patient's femur during a hip revision. FIGS. 8, 9, and 10 depict an example of such a femoral component (which is designated therein as "femoral component 1000"). As FIG. 8 illustrates, the femoral component 1000 is provided with a head 1100, a trunnion axis 1101, and a stem 1200, which includes a stem axis 1201. As FIGS. 8, 9, and 10 further show, the head 1100 (shown in FIG. 8) is disposed on a trunnion 1102 (shown in FIGS. 9 and 10). The trunnion 1102 is generally cylindrical about the trunnion axis 1101 but tapers from the top surface 1103 of the trunnion 1102 to the bottom surface 1104 of the trunnion 1102. The top and bottom surfaces 1103, 1104 are oriented to be generally orthogonal to the trunnion axis 1101.

Extending from the bottom surface 1104 of the trunnion 1102 is a trunnion neck 1300, which is generally co-axial with the axis 1101 of the trunnion 1102 and generally rectangular when cross-sectioned axially. The trunnion neck 1300 of the femoral component 1000 usually tapers to a larger dimension as it blends into an impacted section 1400 (which includes an impacting axis 1401). The impacting axis 1401 generally defines the direction in which the femoral component 1000 is inserted into a patient's femur, and those of ordinary skill in the art will understand that the femoral component 1000 is often provided with a cylindrical hole that is axially parallel with the impacting axis 1401 shown in FIGS. 8 and 9. Such a cylindrical hole is for a tool that is impacted (which thereby impacts the femoral component 1000 into a patient's femur) when the femoral component 1000 is surgically implanted.

As noted above, the body 200 of the extractor 100 is configured to remove from a patient's femur the femoral component (such as the standard femoral component 1000 depicted in FIGS. 8, 9, and 10). FIGS. 11 and 12 illustrate how the body 200 of the extractor 100 is configured to remove the femoral component. FIG. 11 shows the notch 215 of the body 200 accepting at least a portion of the trunnion neck 1300. The arms 212, 213 of the body 200 are dimensioned so that they extend around at least a portion of the trunnion neck 1300 and the upper arm surfaces 216, 218 in contact with the bottom surface 1104 of the trunnion 1102. As FIGS. 11 and 12 illustrate, the arm extension bar 214 extends axially so as to accommodate the axial dimension of the trunnion 1104 between the tightening surface 412 and the upper arm surfaces 216, 218. Thus, the trunnion accepting structure 2102 is configured to accommodate at least a portion of the trunnion 1104.

Figure 13:
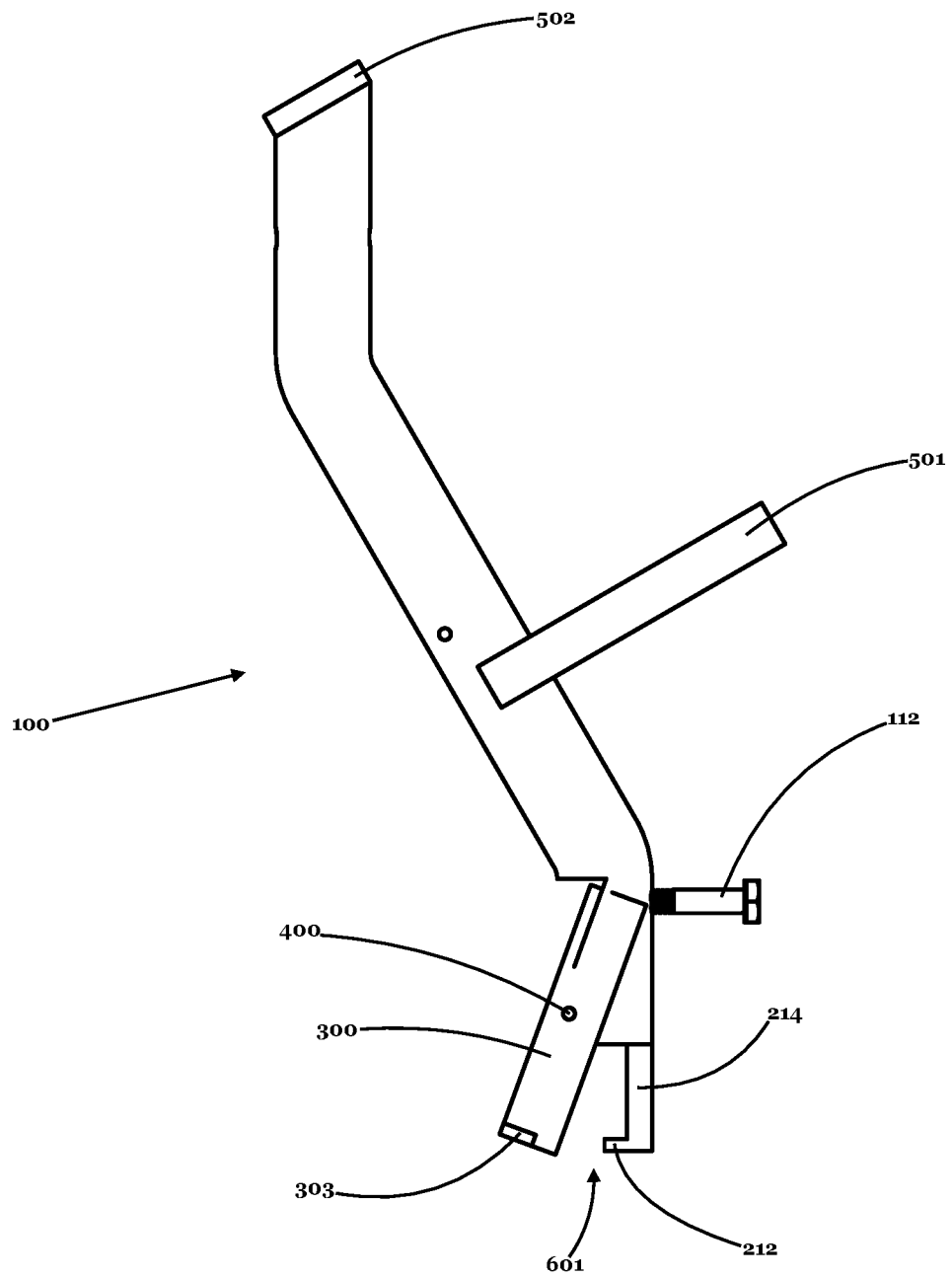
FIG. 13 depicts a perspective view of the extractor with the pivoting member in the fully open position.
Figure 14:
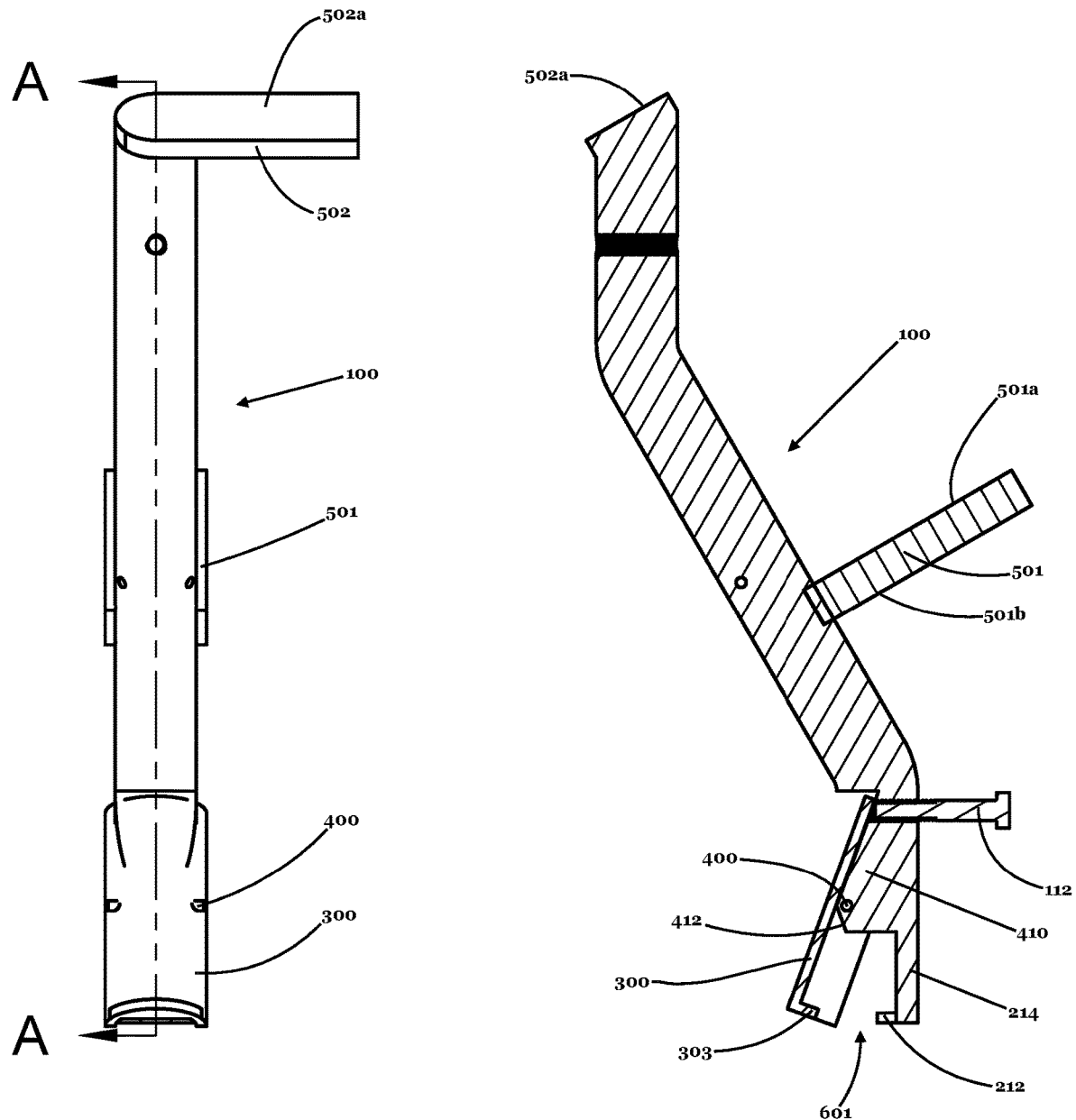
FIG. 14 depicts a sectional view of the extractor with the pivoting member in the fully open position.
Figure 15:
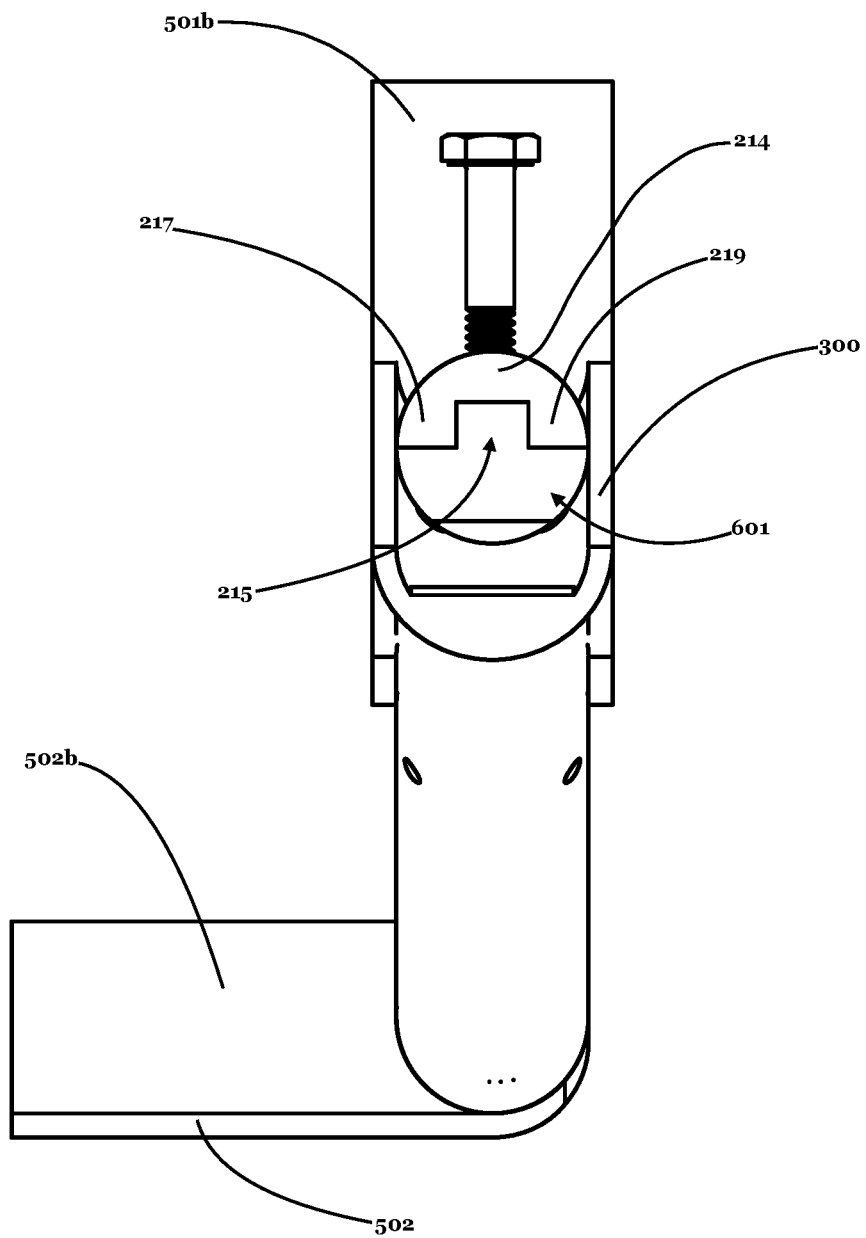
FIG. 15 depicts a perspective view of the opening of the extractor with the pivoting member in the fully open position.

Turning now to FIGS. 13, 14, and 15, the extractor 100 is shown configured to accept the trunnion 1102 of the femoral component 1000. FIG. 13 is a perspective view of the extractor 100 after the pivoting member 300 has been rotated about the pivot 400 so that the axis 301 is generally parallel with the plane of the fulcrum surface 411. FIG. 14 depicts a sectional view of the extractor 100 shown in FIG. 13. FIG. 15 is a perspective view of the opening 601 that is formed when the pivoting member 300 is rotated about the pivot 400 so that the axis 301 is generally parallel with the plane of the fulcrum surface 411. As noted above, and as FIGS. 13, 14, and 15 illustrate, the fulcrum structure 410 is shaped to enable the pivoting member 300 to be rotated so that the axis 301 of the pivoting member 300 approaches a position that is generally parallel with the plane of the fulcrum surface 411. By thus rotating the pivoting member 300 towards the plane of the fulcrum surface 411, the opening 601 is increasingly enlarged to accommodate trunnions of increasing size. Thus, the extractor 100 is provided with an opening 601 that is configured to accept the trunnion 1102 of virtually any femoral component 1000.

Figure 16:
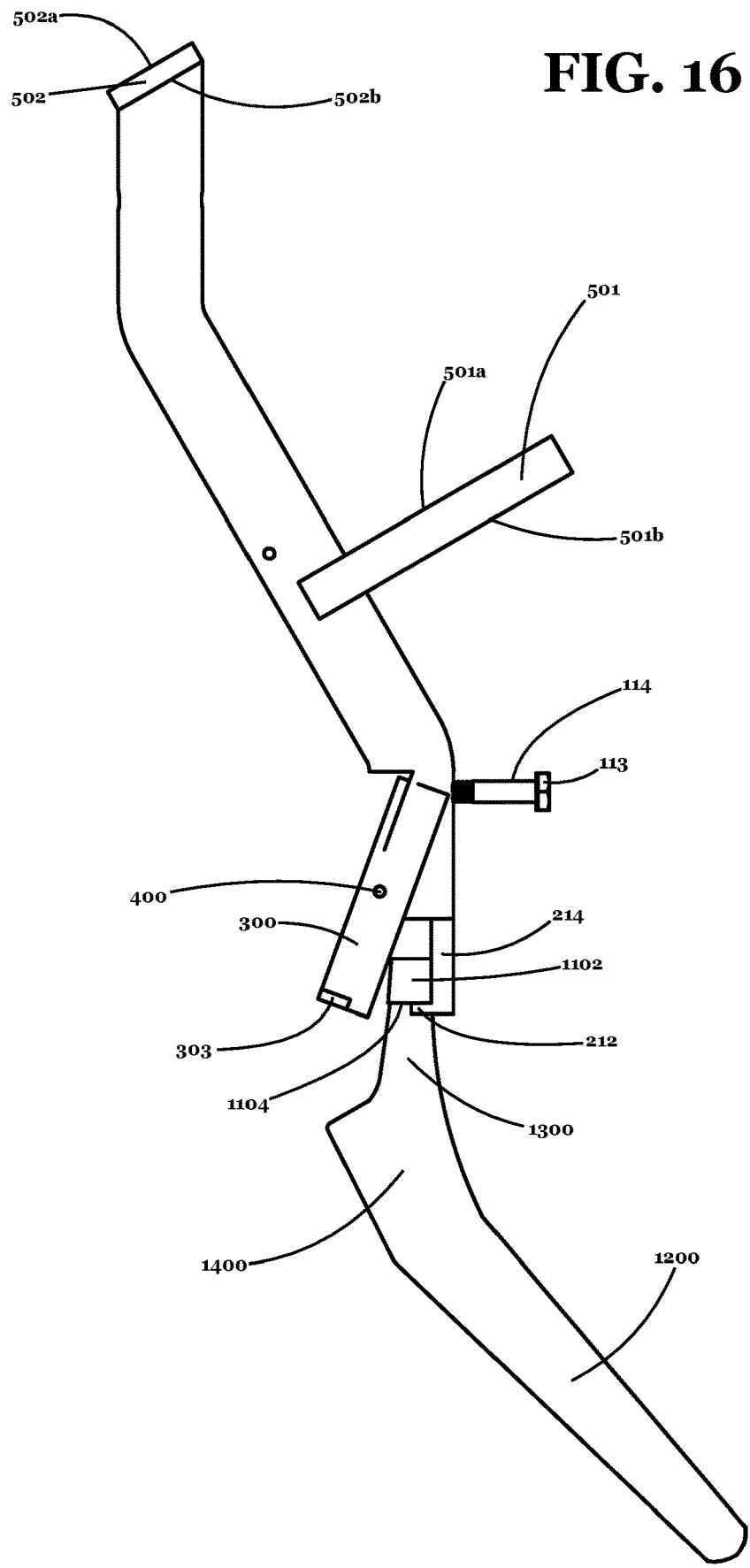
FIG. 16 depicts a perspective view of the extractor with the neck of the femoral component located between the arms of the body.
Figure 17:
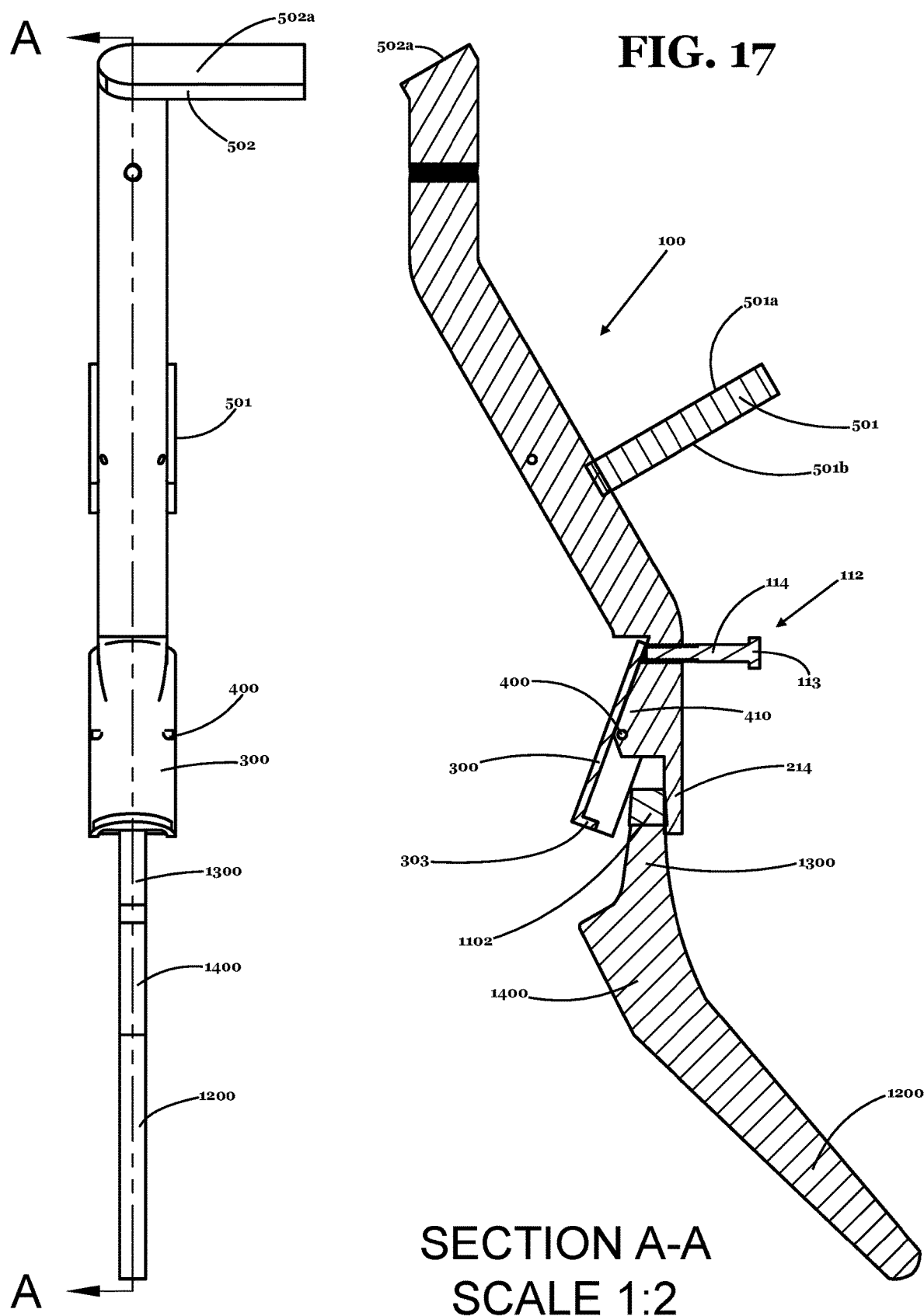
FIG. 17 depicts a sectional view of the extractor with the neck of the femoral component located between the arms of the body.

After the pivoting member 300 is rotated about the pivot 400 so that the axis 301 is generally parallel with the plane of the fulcrum surface 411, the extractor 100 is "opened" so that the trunnion 1102 easily fits through the opening 601. FIGS. 16 and 17 depict the extractor 100 thus opened and accommodating a trunnion 1102 through the opening 601. As FIGS. 16 and 17 demonstrate, the arms 212, 213 are positioned relative to the trunnion 1102 so that the upper arm surfaces 216, 218 contact at least a portion of the bottom surface 1104 of the trunnion 1102. As FIGS. 16 and 17 further show, the trunnion neck 1300 is located within the notch 215 between the arms 212, 213. With the trunnion 1102 thus disposed within the extractor, a force can be exerted upon the bottom surface 1104 of the trunnion 1102.

Figure 18:
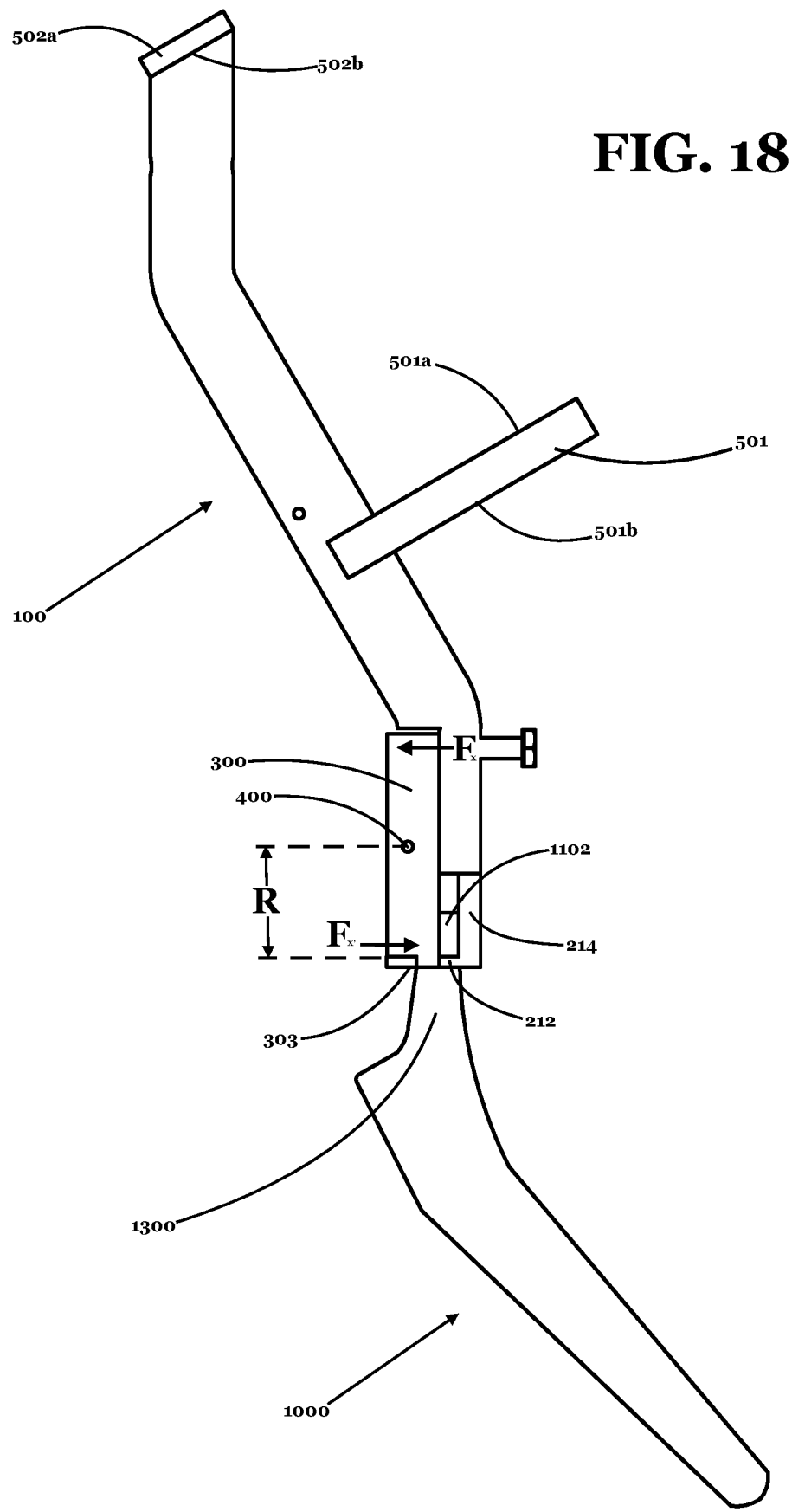
FIG. 18 depicts a perspective view of the extractor with the pivoting member clamping on the neck of the femoral component.
Figure 19:
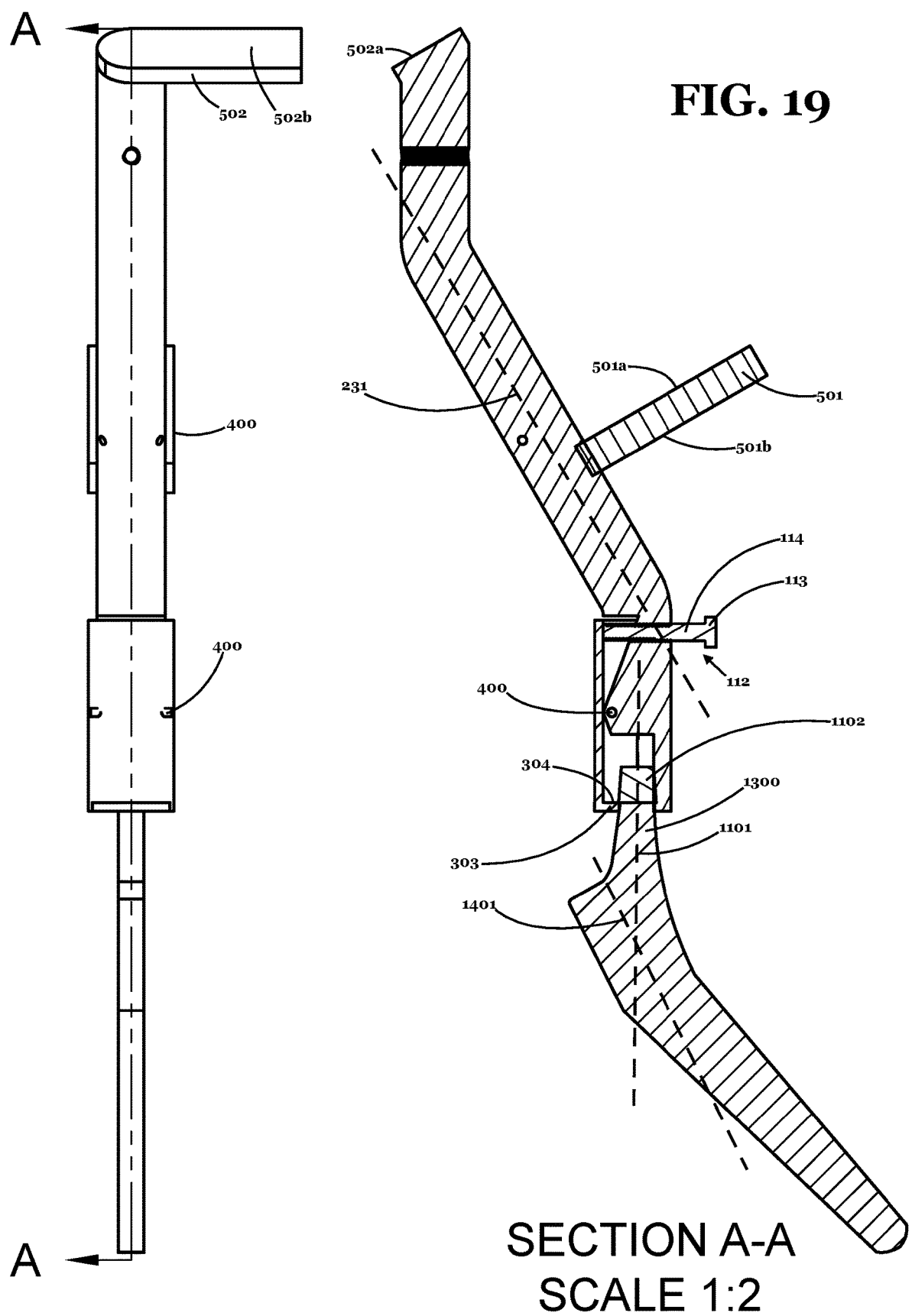
FIG. 19 depicts a sectional view of the extractor with the pivoting member clamping on the neck of the femoral component.

Referring now to FIGS. 18 and 19, the extractor 100 is shown configured to clamp the trunnion neck 1300 securely. After the arms 212, 213 are positioned under the trunnion 1102, it is desirable to torque the threaded component 112 into the threaded hole 413 of the body 200 so as to clamp the femoral component 1000 about the trunnion neck 1300. The threaded component 112 is provided with a torque transferring structure 113 in the form of a hex head and a threaded shank 114. The threaded component 112 is dimensioned so that at least a portion of the threaded shank 114 extends through the threaded hole 413 and contacts the pivoting member 300, preferably the pocket 302. Once the threaded component 112 contacts the pivoting member 300, continued torqueing of the threaded component 112 into the body 200 will exert a force, designated "Fx" in FIG. 18, on the pivoting member 300 at the point of contact. The force, Fx, exerted by the threaded component 112 as it is torqued into the body 200 will cause the pivoting member 300 to rotate about the pivot 400 so that the axis 301 of the pivoting member 300 approaches the plane of the tightening surface 412. As the axis 301 of the pivoting member 300 approaches the plane of the tightening surface 412, the pivoting member 300 contacts the trunnion neck 1300 and, at the point of contact, exerts a force of equal magnitude, but in the opposite direction, as the force applied by the threaded component 112; the force that the pivoting member 300 exerts on the trunnion neck 1300 is designated Fx' ("Fx prime") on FIG. 18. At the point of contact between the pivoting member 300 and the trunnion neck 1300, the pivoting member is provided with the clamping structure 303, as FIGS. 18 and 19 illustrate. Thus, the threaded component 112 uses the threads of the body's threaded hole 413 as leverage to force the clamping structure 303 onto the trunnion neck 1300. As the axis 301 of the pivoting member 300 approaches the plane of the tightening surface 412, the force, Fx', that the clamping structure 303 exerts on the trunnion neck 1300 increases.

In the preferred embodiment, the clamping structure 303 of the pivoting member 300 is dimensioned so that it fits, at least in part, under the trunnion 1102. As noted above, the pivoting member 200 rotates about the pivot 400, and therefore, the inner tooth surface 304 moves in a circle about the pivot 400 with a radius, designated "R" on FIG. 18, that is greater than 0.779 inches. The radius R is dimensioned according to the axial distance between the pivot hole 401 and the upper arm surfaces 216, 218 (which is designated "D" in FIG. 3). The relationship between the dimensions of radius "R" (shown in FIG. 18) and axial distance "D" (shown in FIG. 3) is the following: $R^2=(0.799)^2+D^2$. Thus, the radius R is dimensioned according to the axial distance "D" separating the upper arm surfaces 216, 218 and the pivot hole 401.

As noted above, the inner tooth surface 304 rotates about the pivot 400 at a radius R, and therefore, the clamping structure 303 of the pivoting member 300 also rotates about the pivot 400 at a radius R. As noted above, the radius R is dimensioned so that the clamping structure 303 contacts the trunnion neck 1300 at a location that is generally co-planar with at least one of the arms 212, 213, as FIGS. 18 and 19 depict. The term "generally co-planar" as used in this context means within 1 millimeter of the plane of one of the arms. Thus, the pivoting member 300 is dimensioned so that the clamping structure 303 cooperates with the arms 212, 213 of the body 200. As the threaded component 112 is torqued into the threaded hole 413, the inner tooth surface 304 is forced under the trunnion 1102 and into contact with the bottom surface 1104 of the trunnion 1102; the trunnion neck 1300 is also forced between the arms 212, 213 and into the notch 215, thereby bringing the bottom trunnion surface 1104 into increasing contact with the upper arm surfaces 216, 218 of the arms 212, 213.

Various figures provided herein disclose that the body 200 is provided with a plurality of strike plates 501, 502. The strike plates 501, 502 are oriented to extend from the body 200 so that at least one of the strike plates 501, 502 is generally orthogonal to the impacting axis 1401 of the femoral component 1000. Inn the preferred embodiment, both of the strike plates 501, 502 and both of the lower striking surfaces 501b, 502b are oriented to be orthogonal to the impacting axis 1401 of the femoral component 1000. Thus, a surface of at least one of the strike plates 501, 502 is oriented to be generally orthogonal relative to an axis of the femoral component. In an alternative embodiment, at least one of the striking surfaces 501b, 502b is oriented to be orthogonal to the impacting axis 1401 of the femoral component 1000. In such an alternative embodiment, the lower striking surface 501b of the first strike plate 501 is oriented to be generally orthogonal relative to the impacting axis 1401 while the lower striking surface 502b of the second strike plate 502 is oriented to be orthogonal to the stem axis 1201, or the lower striking surface 502b of the second strike plate 502 can be oriented to be orthogonal relative to the impacting axis 1401 while the lower striking surface 501b of the first strike plate 501 can be oriented to be orthogonal relative to the stem axis 1201. In yet another alternative embodiment, both of the lower striking surfaces 501b, 502b are oriented to be generally orthogonal to the stem axis 1201 (rather than the impacting axis 1401 as is presently preferred). Thus, the strike plates 501, 502, and the surfaces on the strike plates 501, 502 are oriented so that an impact is imparted to the femoral component in the direction of an axis of the femoral component.

As noted above, the clamping section 110 of the extractor 100 is provided with an axis 111. As FIG. 19 illustrates, the axis 111 of the extractor's clamping section 110 is generally parallel to the trunnion axis 1101. Because the bottom surface 1104 of the trunnion 1102 is generally orthogonal to the trunnion axis 1101, and because the axis 111 of the clamping section 110 is generally parallel with the trunnion axis 1101, the bottom surface 1104 of the trunnion 1102 is generally orthogonal to the axis 111 of the clamping section 110 of the extractor 100. Thus, the clamping section 110 of the extractor is oriented according to the trunnion axis 1101 of the femoral component.

As is also noted above, the extractor 100 is provided with a central extractor section 130 and a central axis 131. Similarly, the body 200 is also provided with a central body section 230 with a central body axis 231. Both the central axis 131 of the extractor 100 and the central body axis 231 are generally co-axial, as are the axes 111, 211 of the extractor 100 and the extractor body 200. The central axes 131, 231 are oriented at an angle relative to the axes 111, 211 of the extractor's clamping section 110 and the body's clamping section 210 that is substantially equal to the angle between the trunnion axis 1101 that is equal in to the angle between the trunnion axis 1101 and the impacting axis 1401. In the embodiment shown herein, this angle ranges between 130 and 150 degrees inclusively, preferably 130 degrees. Thus, the angle between the central axis 131 and the axis 111 of the clamping section 110 is substantially the same as the angle between the trunnion axis 1101 and the impacting axis 1401. One of ordinary skill in the art will appreciate that the angle between the axes 111, 211 of the central sections of the extractor 100 and the body 200 respectively are can be substantially equal to the angle between the trunnion axis 1401 and the stem axis 1201 without departing from the spirit of the present invention. As used in the context of the angles between the various axes of the extractor and the body, the term "substantially" means within a margin of variance in manufacturing and use that is 10%.

One of ordinary skill in the art will understand that the extractor 100 can be used with a slap hammer or a mallet. A slap hammer (not shown) can be attached to one of the strike places 501, 502 such as by screwing a slap hammer shaft into an internal thread tapped into the plates 501 502. In such an arrangement, the slap hammer extends from one of the upper striking surface 501*a*, 502*a* at an angle that is generally orthogonal to the strike plates 501, 502 (and hence parallel to the orientation of the impacting axis 1401 of the femoral component 1000). Thus, when the slap hammer is employed, the femoral component 1000 is removed from a patient's femur at substantially the same angle as it was inserted. A mallet can be used by striking one of the lower striking surfaces 501*b*, 502*b* and removing the femoral component 1000 at substantially the same angle as it was originally impacted into the femur.

Though the preferred embodiment is provided with upper striking surfaces 501*a*, 502*a* and lower striking surfaces 501*b*, 502*b* that are generally parallel with each other and generally orthogonal to the impacting axis 1401 of the femoral component 1000, alternative embodiments are provided with upper striking surfaces 501*a*, 502*a* and lower striking surfaces 501*b*, 502*b* that are generally orthogonal to the stem axis 1201. In yet another alternative embodiment, one of the strike plates 501, 502 is orthogonal to the impacting axis 1401 while the other is orthogonal to the stem axis 1201. In such an arrangement, a mallet can be used to strike the strike plate that is generally orthogonal to the tem axis 1201 while a slap hammer is attached to the other strike plate at an angle that is orthogonal to the impacting axis 1401. One of ordinary skill in the art will appreciate that the foregoing arrangement can be reversed with the slap hammer attached to one of the strike plates 501, 502 at an angle that is generally orthogonal to the stem axis 1201 while the other strike plate is oriented at an angle that is generally orthogonal to the impacting axis 1401.

Figure 20:
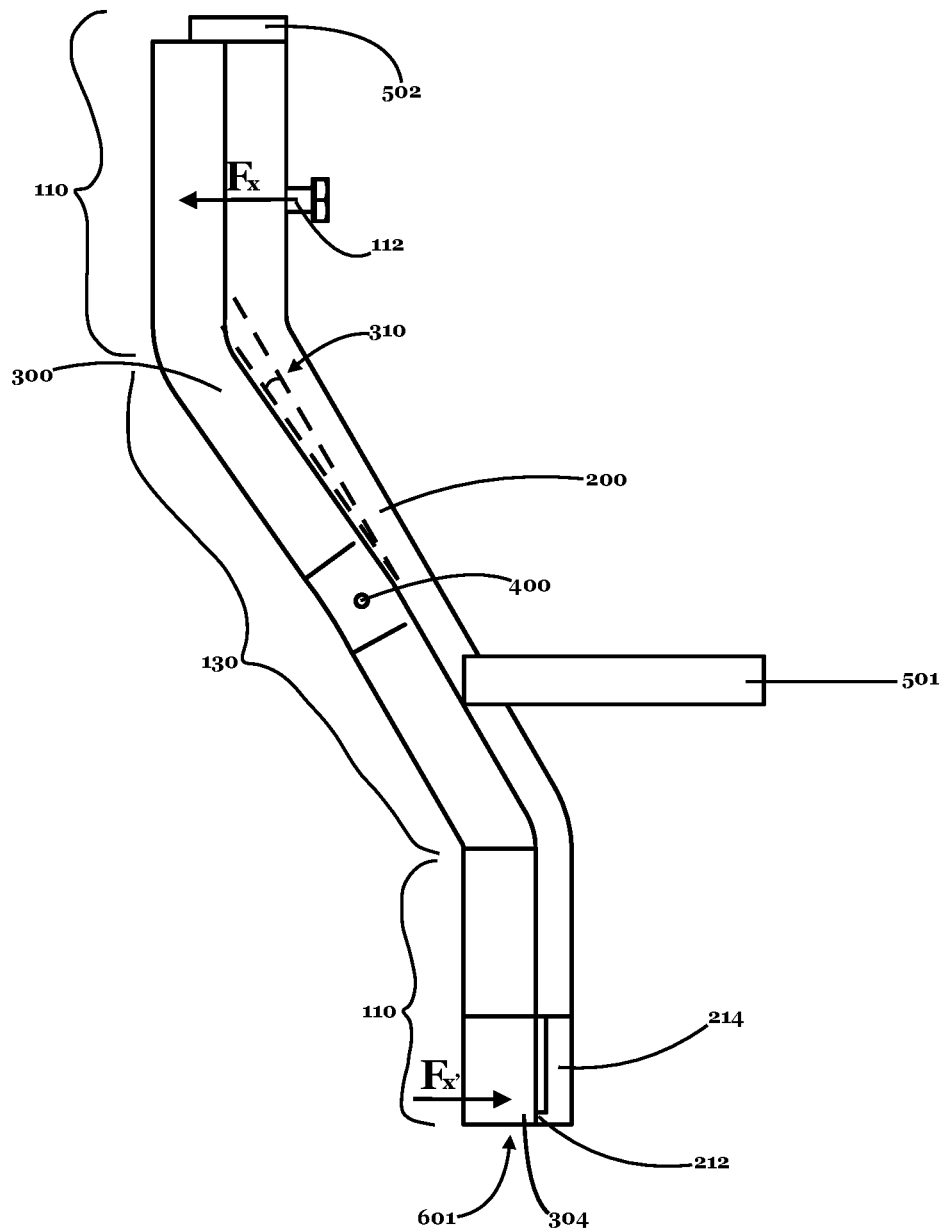
FIG. 20 depicts a perspective view of an alternative embodiment of the extractor.
Figure 21:
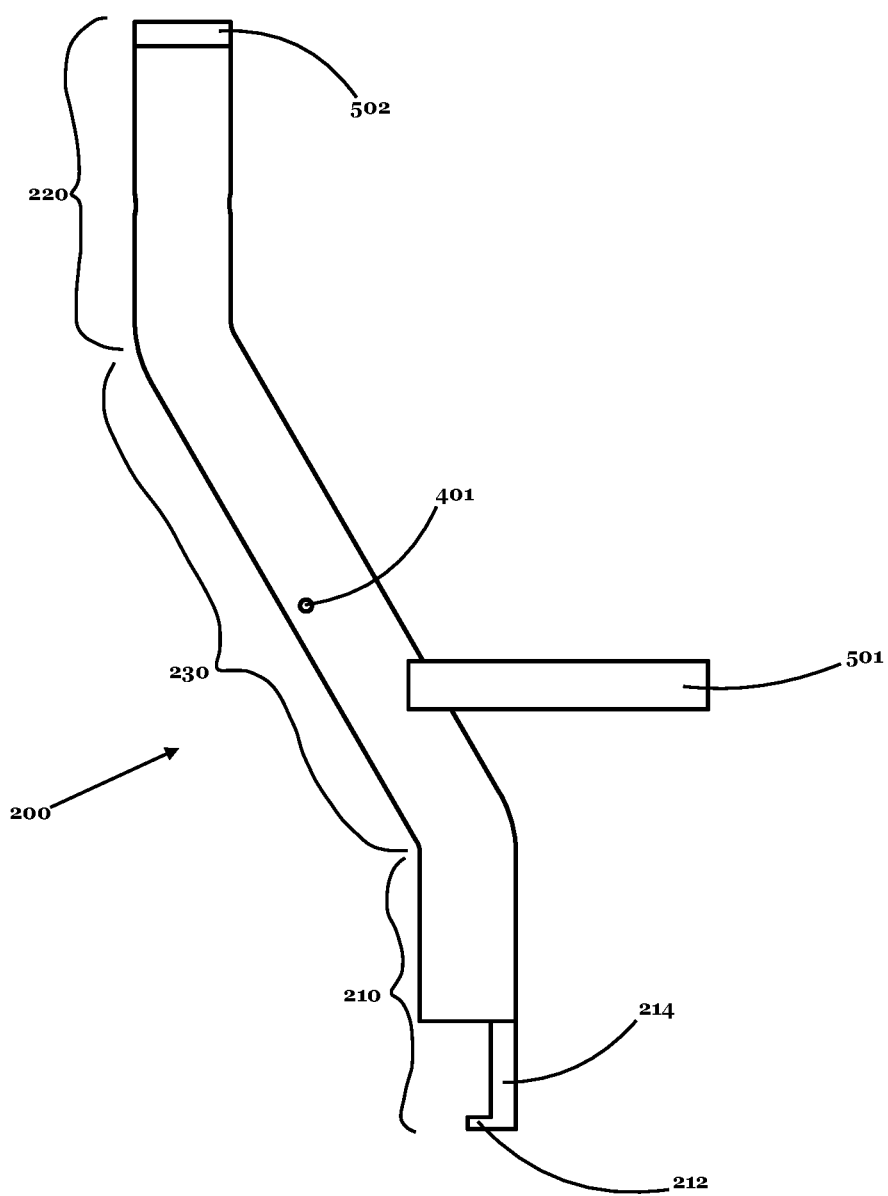
FIG. 21 depicts a perspective view of an alternative embodiment of the body of the extractor shown in FIG. 20.

FIGS. 20 and 21 depict an alternative embodiment of the present invention. As shown therein, the extractor 100 includes a first section 110 (also referred to as a "clamping section 110"), a second section 120 (also referred to as an "upper section"), and a third section 130 (also referred to as a "central section"). The extractor is also provided with a body 200, a pivoting member 300, and a pivot 400.

Figure 22:
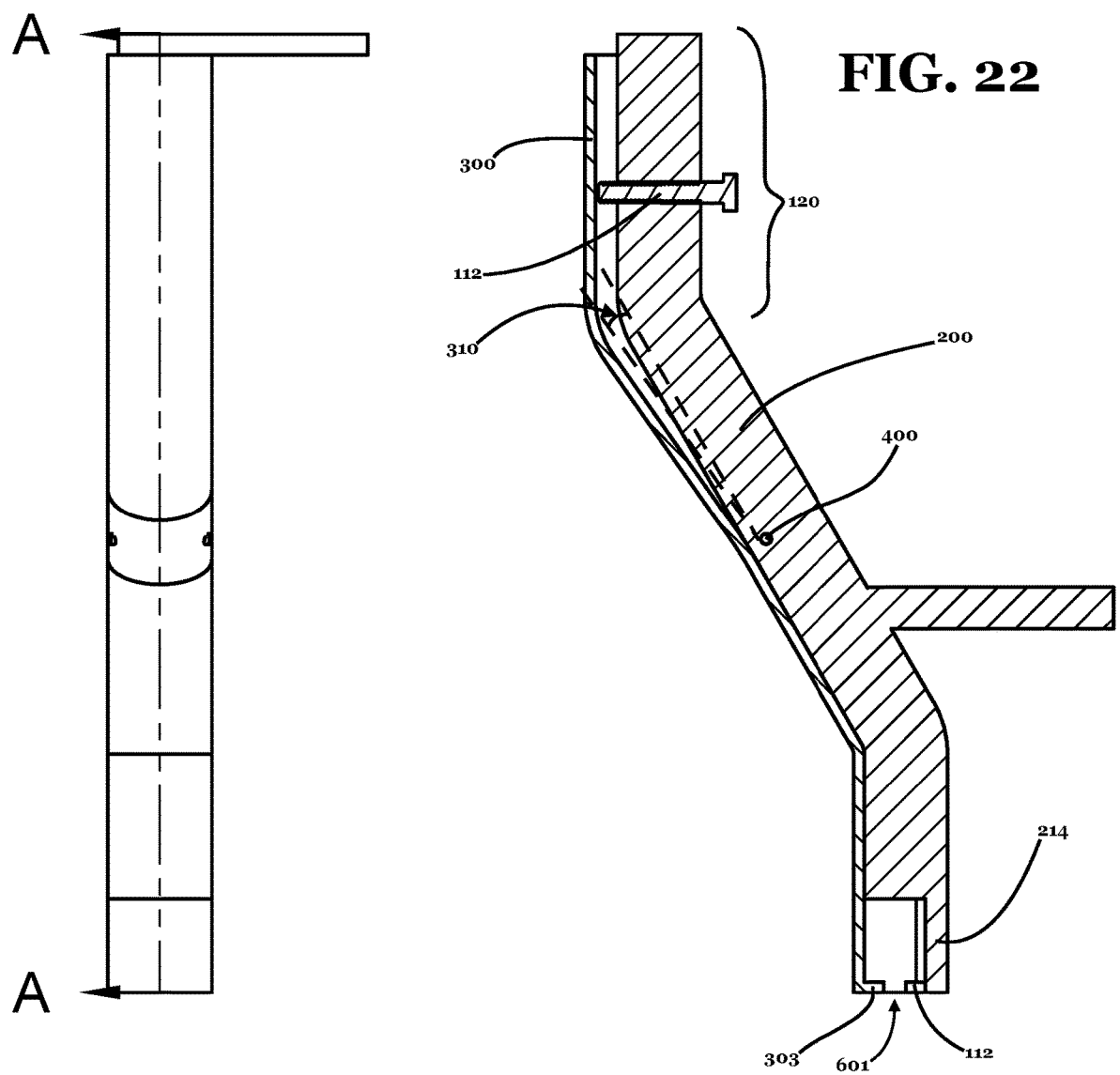
FIG. 22 depicts a sectional view of the alternative embodiment of the extractor shown in FIG. 20.
Figure 23:
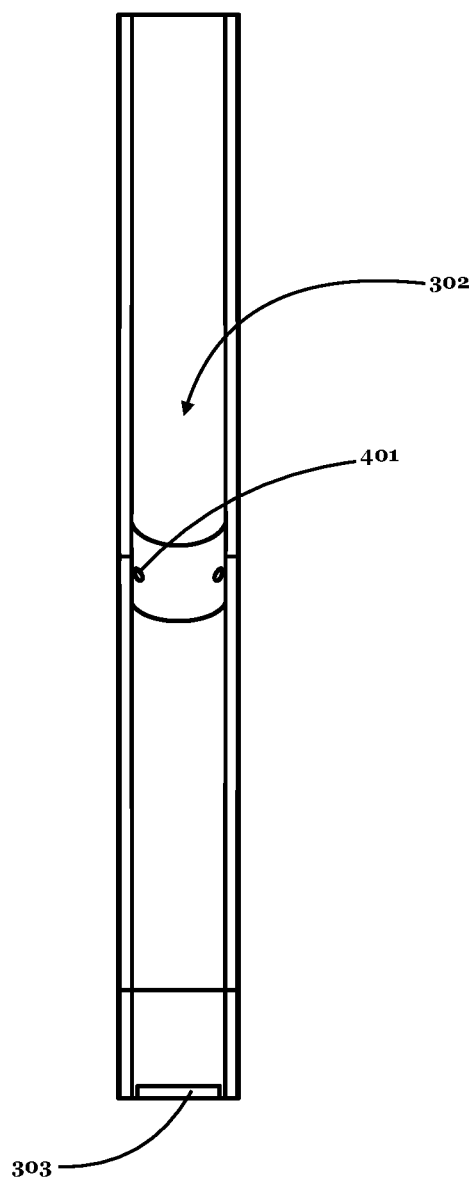
FIG. 23 depicts a perspective view of the alternative embodiment of the pivoting member of the extractor shown in FIG. 20.

The body 200 of the alternative embodiment shown in FIG. 20 is depicted in FIG. 22 and is largely the same as the body 200 disclosed as the presently preferred embodiment. As shown in FIG. 22, the body 200 is provided with a first body section 210 (also referred to as the "clamping body section 210"), a second body section 220 (also referred to as the "impacting body section 220") and a third body section 230 (also referred to as the "central body section 230"). However, unlike the pivoting member 300 in the preferred embodiment, the pivoting member 300 of the alternative embodiment shown in FIGS. 20 and 21 extends substantially the entire length of the body 200 and terminates within the upper section 120 of the extractor 100 under the second strike plate 502. Additionally, unlike the preferred embodiment, the pivot hole 401 in FIGS. 20 and 21 is defined within the central body section 230, and the threaded hole 413 is defined within the upper body section 220.

As FIG. 20 depicts, the pivoting member 300 is provided with a pivoting angle 310. By the virtue of the pivoting angle 310, a surgeon can squeeze the upper section 120 of the extractor 100 and thereby force the pivoting member 300 and the body 200 together at the upper section 120. By forcing the pivoting member 300 and the body together at the upper section 120, the surgeon forces the clamping structure 303 away from the arms 212 of the body 200 at the opening 601. Thus, the opening 601 of the extractor 100 is enlarged.

Much like the preferred embodiment, the alternative embodiment shown in FIGS. 20, 21, and 22 is provided with a threaded component 112 that is dimensioned so that at least a portion of the threaded shank 114 extends through the threaded hole 413 and contacts the pivoting member 300, preferably the pocket 302. Once the threaded component 112 contacts the pivoting member 300, continued torqueing of the threaded component 112 into the body 200 in the direction of Fx will cause the pivoting member 300 to rotate about the pivot 400 (counter clockwise as shown in FIG. 20) so that the clamping structure 304 rotates towards the trunnion neck 1300. Thus, as the threaded component 112 is torqued into the body 200, the pivoting member 300 exerts a greater clamping force on the trunnion neck 1300. Much like the preferred embodiment, in the alternative embodiment shown in FIGS. 20, 21, and 22 the threaded component 112 uses the threads of the body's threaded hole 413 as leverage to force the clamping structure 303 onto the trunnion neck 1300.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An extractor for a femoral component, the femoral component with a trunnion with a top surface, a bottom surface, and a trunnion neck, the extractor comprising,
   a) a body with a threaded hole and a pivot hole, the threaded hole and the pivot hole being defined within the body, and the body further including a clamping body section, wherein:
      i) the threaded hole extends orthogonally into the body relative to the pivot hole;
      ii) the clamping body section is provided with a first arm and a second arm wherein the arms are spaced from each other so as to define a notch that is dimensioned to accept, at least in part, the trunnion neck of the femoral component;
      iii) the arms are provided with upper arm surfaces that are dimensioned to extend around at least a portion of the trunnion neck and contact the bottom surface of the trunnion;
   b) a pivot that secures a pivoting member to the body by extending through a member pivot hole defined in the pivoting member and the pivot hole defined in the body;
   c) the pivoting member is provided with a first end and a second end and further includes:
      i) a clamping structure located at the second end and shaped to clamp the trunnion neck of the femoral component;

ii) the clamping structure is provided with a tooth with an inner tooth surface;

iii) the pivot hole of the pivoting member is positioned so that the clamping structure rotates about the pivot whereby:

(1) the inner tooth surface of the clamping structure is positioned to contact the bottom surface of the trunnion;

(2) the body of the extractor is positioned so that the trunnion neck is between the arms and at least partially within the notch, and (3) the upper arm surfaces of the body are positioned with respect to the trunnion so that the upper arm surfaces contact the bottom trunnion surface;

d) a threaded member with a shank that is has been torqued into the threaded hole of the body; and e) the shank of the threaded member is dimensioned to extend into the threaded hole of the body so that the threaded member contacts the pivoting member at the first end.

2. An extractor according to claim 1 wherein the arms further include lower arm surfaces that are co-planar to each other.

3. An extractor according to claim 1 further comprising a trunnion accepting structure, and an arm extension bar that includes a plurality of upper arm surfaces, wherein the trunnion accepting structure is dimensioned so that:

a) the top surface of the trunnion fits within the trunnion accepting structure, and b) the bottom surface of the trunnion contacts the upper arm surfaces.

4. An extractor according to claim 1 wherein the arms are generally co-planar with each other.

5. An extractor according to claim 1 wherein the clamping structure of the pivoting member rotates to a position that is generally co-planar with at least one of the arms.

6. An extractor according to claim 1 wherein the femoral component further includes an impacting axis and the extractor further comprises a strike plate that is provided with a striking surface wherein, the striking surface of the strike plate is oriented to be orthogonal relative to the impacting axis of the femoral component.

7. An extractor according to claim 1 wherein the femoral component further includes a stem axis and the extractor further comprises a strike plate that is provided with a striking surface wherein the striking surface of the strike plate is oriented to be orthogonal relative to the stem axis of the femoral component.

8. An extractor for a femoral component, the femoral component including a trunnion neck, the extractor comprising, a) a body with a threaded hole defined therein b) the body is provided with a clamping body section, a fulcrum structure, and a central body section wherein:

i. the clamping body section is provided with a pair of arms that are generally co-planar with each other and extend from an arm extension bar so as to define a notch thereinbetween;

ii. the notch is dimensioned to accept, at least in part, the trunnion neck of the femoral component;

iii. the fulcrum structure is provided with a pivot hole defined therein;

iv. the threaded hole is generally orthogonal relative to the pivot hole of the fulcrum structure;

a. a pivoting member with first end, a second end, and a member pivot hole defined thereinbetween that includes a clamping structure located at the second end that is provided with a tooth that is shaped to clamp the trunnion neck of the femoral component;

b. a pivot that secures the pivoting member to the body by extending through the member pivot hole defined in the pivoting member and the pivot hole defined in the fulcrum structure of the body;

c. a threaded member with a shank that is has been torqued into the threaded hole of the body; and d. the shank of the threaded member extends into the threaded hole of the body so that the threaded member contacts the first end of the pivoting member.

9. An extractor according to claim 8 wherein the arms further include lower arm surfaces that are co-planar to each other.

10. An extractor according to claim 8 wherein the body further comprises a trunnion accepting structure wherein the arm extension bar extends axially and the arms extend radially so that the top and bottom surfaces of the trunnion fit within the trunnion accepting structure.

11. An extractor according to claim 8 wherein the clamping structure of the pivoting member rotates to a position that is generally co-planar with at least one of the arms.

12. An extractor according to claim 8 wherein the femoral component includes an impacting axis and the extractor further comprises a strike plate that is provided with a striking surface that is oriented to be orthogonal relative to the impacting axis of the femoral component.

13. An extractor according to claim 8 wherein the femoral component includes a stem axis and the extractor further comprises a strike plate that is provided with a striking surface that is oriented to be orthogonal relative to the stem axis of the femoral component.

14. An extractor for a femoral component, the femoral component including a trunnion neck, the extractor comprising, a) a plurality of extractor sections, including an upper section and a clamping section;

b) a body with a pivot hole and a threaded hole defined therein, the body further provided with a clamping body section, a central body section, and an impacting body section wherein:

i) the clamping body section of the body includes a trunnion accepting structure;

ii) the threaded hole extends into the body in an orientation that is generally orthogonal relative to the pivot hole;

c) a pivoting member with a pivot hole defined therein, further comprising a first end, and a second end wherein the first end is located in the upper section of the extractor while the second end is located in the clamping section of the extractor and includes a clamping structure shaped to clamp the trunnion neck of the femoral component;

d) a pivot that secures the pivoting member to the body by extending through the pivot hole defined in the pivoting member and the pivot hole defined in the central body section;

e) a threaded member with a shank that is has been torqued into the threaded hole of the body; and f) the shank of the threaded member is dimensioned to extend through the threaded hole of the body and contact the pivoting member at the first end.

15. An extractor according to claim 14 wherein the pivoting member further comprises a tooth and the body further comprises a pair of arms that define a notch thereinbetween.

16. An extractor according to claim 15 wherein the arms further include lower arm surfaces that are co-planar to each other.

17. An extractor according to claim 15 wherein the clamping structure of the pivoting member rotates to a position that is generally co-planar with at least one of the arms.

18. An extractor according to claim 15 wherein the femoral component includes a top surface and a bottom surface and the body further comprises a trunnion accepting structure and an arm extension bar wherein the arm extension bar extends axially so that the top and bottom surfaces of the trunnion fit within the trunnion accepting structure.

19. An extractor according to claim 14 wherein the femoral component is further provided with an impacting axis and the extractor further comprises a strike plate that includes a striking surface that is oriented to be orthogonal relative to the impacting axis of the femoral component.

20. An extractor according to claim 14 wherein the femoral component is further provided with a stem axis and the extractor further comprises a strike plate that includes a striking surface that is oriented to be orthogonal relative to the stem axis of the femoral component.

21. An extractor for a femoral component, the femoral component including a trunnion with a bottom surface, and a trunnion neck, the extractor comprising,
 a) a plurality of extractor sections, including an upper section, a central section, and a clamping section;
 b) a strike plate is located in at least one of the upper section or the central section of the extractor;
 c) the clamping section of the extractor is provided with a pivot hole and a threaded hole for a threaded member;
  i) the clamping section of the extractor further includes a trunnion accepting structure;
  ii) the threaded member is oriented to extend from the extractor and engage the threaded hole in an orientation that is generally orthogonal relative to the pivot hole;
 d) the clamping section of the extractor further includes a pivoting member with a pivoting member hole defined therein and a clamping structure shaped to clamp the trunnion neck of the femoral component;
 e) the clamping structure of the pivoting member includes a tooth with an inner tooth surface that is positioned to contact the bottom surface of the trunnion;
 f) a pivot that secures the pivoting member to the body by extending through the pivoting member hole defined in the pivoting member and the pivot hole defined in the central body section; and
 g) the tooth of the pivoting member clamps the trunnion neck of the femoral component when the threaded member has been torqued into the threaded hole located in the clamping section of the extractor.

22. An extractor according to claim 21 wherein the clamping section of the extractor further comprises a pair of arms that define a notch thereinbetween.

23. An extractor according to claim 22 wherein the arms further include lower arm surfaces that are co-planar to each other.

24. An extractor according to claim 22 wherein the clamping structure of the pivoting member rotates to a position that is generally co-planar with at least one of the arms.

25. An extractor according to claim 21 wherein the trunnnion further includes a top surface and the clamping section of the extractor further comprises a trunnion accepting structure and an arm extension bar wherein the arm extension bar is dimensioned so that the top and bottom surfaces of the trunnion fit within the trunnion accepting structure.

* * * * *